FIG. 3A

United States Patent [19]
Wasmoen et al.
[11] Patent Number: 5,989,562
[45] Date of Patent: Nov. 23, 1999
[54] RECOMBINANT RACCOON POX VIRUSES AND THEIR USE AS AN EFFECTIVE VACCINE AGAINST FELINE IMMUNODEFICIENCY VIRUS INFECTION
[75] Inventors: Terri Wasmoen; Hsien-Jue Chu, both of Fort

```
         10         20         30         40         50         60
          *          *          *          *          *          *
GGATCCAACA ATAATTATGG CAGAAGGATT TGCAGCCAAT AGACAATGGA TAGGACCAGA
CCTAGGTTGT TATTAATACC GTCTTCCTAA ACGTCGGTTA TCTGTTACCT ATCCTGGTCT
                   M  A  E  G  F  A  A  N  R  Q  W  I  G  P  E>

70         80         90        100        110        120
          *          *          *          *          *          *
AGAAGCTGAA GAGTTATTAG ATTTTGATAT AGCAACACAA ATGAATGAAG AAGGGCCACT
TCTTCGACTT CTCAATAATC TAAAACTATA TCGTTGTGTT TACTTACTTC TTCCCGGTGA
 E  A  E  L  L  D  F  D  I  A  T  Q  M  N  E  E  G  P  L>

130        140        150        160        170        180
          *          *          *          *          *          *
AAATCCAGGG ATGAACCCAT TTAGGGTACC TGGAATAACA GATAAAGAAA AGCAAGACTA
TTTAGGTCCC TACTTGGGTA AATCCCATGG ACCTTATTGT CTATTTCTTT TCGTTCTGAT
 N  P  G  M  N  P  F  R  V  P  G  I  T  D  K  E  K  Q  D  Y>

190        200        210        220        230        240
          *          *          *          *          *          *
TTGTAACATA TTACAACCTA AGTTACAAGA TTTACGGAAT GAACTTCAAG AGGTAAAAACT
AACATTGTAT AATGTTGGAT TCAATGTTCT AAATGCCTTA CTTGAAGTTC TCCATTTTGA
 C  N  I  L  Q  P  K  L  Q  D  L  R  N  E  L  Q  E  V  K  L>
```

FIG. 3B

```
        250         260         270         280         290         300
         *           *           *           *           *           *
AGAAGAAGGA AATGCAGGTA AGTTTAGAAG AACAAGATTT TTAAGGTATT CTGATGAACA
TCTTCTTCCT TTACGTCCAT TCAAATCTTC TTGTTCTAAA AATTCCATAA GACTACTTGT
 E  E  G    N  A  G    K  F  R  R    T  R  F    L  R  Y    S  D  E  Q>

310         320         330         340         350         360
         *           *           *           *           *           *
AGTATTGTCC CCGGTTCATG CGTTCATAGG ATATTGTATT TATTTAGGTA ATCGAAATAA
TCATAACAGG GGCCAAGTAC GCAAGTATCC TATAACATAA ATAAATCCAT TAGCTTTATT
 V  L  S    P  V  H    A  F  I  G    Y  C  I    Y  L  G    N  R  N  K>

370         380         390         400         410         420
         *           *           *           *           *           *
GTTAGGATCT TTAAGACATG ACATTGATAT TGAAGCACCC CCCGAAGAGT GTTATGATAA
CAATCCTAGA AATTCTGTAC TGTAACTATA ACTTCGTGGG GGGCTTCTCA CAATACTATT
 L  G  S    L  R  H    D  I  D  I    E  A  P    P  E  E    C  Y  D  N>

430         440         450         460         470         480
         *           *           *           *           *           *
                                                        AvrII
TAGAGAGAAG GGTACAACTG ACAATATAAA ATATGGTAGA CGATGTTGCC TAGGAACGGT
ATCTCTCTTC CCATGTTGAC TGTTATATTT TATACCATCT GCTACAACGG ATCCTTGCCA
 R  E  K    G  T  T    D  N  I  K    Y  G  R    R  C  C    L  G  T  V>
```

FIG. 3C

```
         490        500        510        520        530        540
          *          *          *          *          *          *
GACTTGTAC CTGATTTTAT TTATAGGATT AATAATATAT TCACAGACAG CCGACGCTCA
CTGAAACATG GACTAAAATA AATATCCTAA TTATTATATA AGTGTCTGTC GGCTGCGAGT
 T  L  Y   L  I  L   F  I  G  L   I  I  Y   S  Q  T   A  D  A  Q>

550        560        570        580        590        600
          *          *          *          *          *          *
GGTAGTATGG AGACTTCCAC CATTAGTAGT CCCAGTAGAA GAATCAGAAA TAATTTTTTG
CCATCATACC TCTGAAGGTG GTAATCATCA GGGTCATCTT CTTAGTCTTT ATTAAAAAAC
 V  V  W   R  L  P   P  L  V  V   P  V  E   E  S  E   I  I  F  W>

610        620        630        640        650        660
          *          *          *          *          *          *
GGATTGTTGG GCACCAGAAG AACCCGCCTG TCAGGACTTT CTTGGGGCAA TGATACATCT
CCTAACAACC CGTGGTCTTC TTGGGCGGAC AGTCCTGAAA GAACCCCGTT ACTATGTAGA
 D  C  W   A  P  E   E  P  A  C   Q  D  F   L  G  A   M  I  H  L>

670        680        690        700        710        720
          *          *          *          *          *          *
AAAAGCTAAG ACAAATATAA GTATACGAGA GGGACCTACC TTGGGGAATT GGGCTAGAGA
TTTCGATTC TGTTTATATT CATATGCTCT CCCTGGATGG AACCCCTTAA CCCGATCTCT
 K  A  K   T  N  I   S  I  R  E   G  P  T   L  G  N   W  A  R  E>
```

FIG. 3E

```
          970         980         990        1000        1010        1020
           *           *           *           *           *           *
      ACAATTAAGC TATTGTACAG ACCCATTACA AATCCCACTG ATCAATTATA CATTTGGACC
      TGTTAATTCG ATAACATGTC TGGGTAATGT TTAGGGTGAC TAGTTAATAT GTAAACCTGG
       Q  L  S   Y  C  T    D  P  L  Q   I  P  L    I  N  Y    T  F  G  P>

1030        1040        1050        1060        1070        1080
           *           *           *           *           *           *
      TAATCAAACA TGTATGTGGA ATACTTCACA AATTCAGGAC CCTGAAATAC CACAATGTGG
      ATTAGTTTGT ACATACACCT TATGAAGTGT TTAAGTCCTG GGACTTTATG GTGTTACACC
       N  Q  T   C  M  W    N  T  S  Q   I  Q  D    P  E  I    P  Q  C  G>

1090        1100        1110        1120        1130        1140
           *           *           *           *           *           *
      ATGGTGGAAT CACATGGCCT ATTATAAACAG TTGTAAATGG GAAGAGGCAA AGGTAAAGTT
      TACCACCTTA GTGTACCGGA TAATATTGTC AACATTACC CTTCTCCGTT TCCATTTCAA
       W  W  N   H  M  A    Y  Y  N  S   C  K  W    E  E  A    K  V  K  F>

1150        1160        1170        1180        1190        1200
           *           *           *           *           *           *
      TCATTGTCAA AGAACACAGA GTCAGCCTGG GTCATGGCGT AGAGCAATCT CGTCATGGAA
      AGTAACAGTT TCTTGTGTCT CAGTCGGACC CAGTACCGCA TCTCGTTAGA GCAGTACCTT
       H  C  Q   R  T  Q    S  Q  P  G   S  W  R    A  I  S    S  W  K>
```

FIG. 3F

```
         1210       1220       1230       1240       1250       1260
          *          *          *          *          *          *
    ACAAGAAAT AGATGGGAGT GGAGACCAGA TTTTGAGAGT GAAAAGGTGA AAATATCTCT
    TGTTTCTTTA TCTACCCTCA CCTCTGGTCT AAAACTCTCA CTTTTCCACT TTTATAGAGA

Q  R  N   R  W  E   W  R  P  D   F  E  S   E  K  V   K  I  S  L>

1270       1280       1290       1300       1310       1320
          *          *          *          *          *          *
    ACAGTGCAAT AGCACGAAAA ACCTAACCTT TGCAATGAGA ACGTTACTCT AGTTCAGGAG ATTATGGAGA
    TGTCACGTTA TCGTGCTTTT TGGATTGGAA ACGTTACTCT TCAAGTCCTC TAATACCTCT

Q  C  N   S  T  K   N  L  T  F   A  M  R   S  S  G   D  Y  G  E>

1330       1340       1350       1360       1370       1380
          *          *          *          *          *          *
    AGTAACGGGA GCTTGGATAG AGTTTGGATG TCATAGAAAT AAATCAAACC TTCATACTGA
    TCATTGCCCT CGAACCTATC TCAAACCTAC AGTATCTTTA TTTAGTTTGG AAGTATGACT

V  T  G   A  W  I   E  F  G  C   H  R  N   K  S  N   L  H  T  E>

1390       1400       1410       1420       1430       1440
          *          *          *          *          *          *
    AGCAAGGTTT AGAATTAGAT GTAGATGGAA TGTAGGGAGT GATACCTCGC TCATTGATAC
    TCGTTCCAAA TCTTAATCTA CATCTACCTT ACATCCCTCA CTATGGAGCG AGTAACTATG

```
        1450       1460       1470       1480       1490       1500
          *          *          *          *          *          *
    ATGTGGAAAC ACTCCAAATG TTTCAGGTGC GAATCCTGTA GATTGTACCA TGTATTCAAA
    TACACCTTTG TGAGGTTTAC AAAGTCCACG CTTAGGACAT CTAACATGGT ACATAAGTTT
     C  G  N    T  P  N    V  S  G  A  N  P  V   D  C  T   M  Y  S  N>

1510       1520       1530       1540       1550       1560
          *          *          *          *          *          *
    TAAAATGTAC AAGTTTCTT TACCAAACGG GTTTACAATG AAGGTAGATG ACCTTATTAT
    ATTTTACATG TTCAAAAGAA ATGGTTTGCC CAAATGTTAC TTCCATCTAC TGGAATAATA
     K  M  Y   K  F  S    L  P  N  G  F  T  M    K  V  D   D  L  I  M>

1570       1580       1590       1600       1610       1620
          *          *          *          *          *          *
    GCATTTCAAT ATGCCAAAAG CTGTAGAAAT GAATAATATT GCTGGAAATT GGTCTTGTAC
    CGTAAAGTTA TACGGTTTTC GACATCTTTA CTTATTATAA CGACCTTTAA CCAGAACATG
     H  F  N    M  P  K   A  V  E  M  N  N  I    A  G  N    W  S  C  T>

1630       1640       1650       1660       1670       1680
          *          *          *          *          *          *
    ATCTGACTTG CCATCGTCAT GGGGTATAT GAATTGTAAT TGCCCAAATA GTAGTAGTAG
    TAGACTGAAC GGTAGCAGTA CCCCCATATA CTTAACATTA ACGGGTTTAT CATCATCATC
     S  D  L   P  S  S    W  G  Y  M  N  C  N    C  P  N    S  S  S  S>
```

FIG. 3H

```
        1690       1700       1710       1720       1730       1740
          *          *          *          *          *          *
TTATAGTGGT ACTAAAATGG CATGTCCTAG CAATCGAGGC ATCTTAAGGA ATTGGTATAA
AATATCACCA TGATTTTACC GTACAGGATC GTTAGCTCCG TAGAATTCCT TAACCATATT
 Y  S  G   T  K  M   A  C  P  S   N  R  G   I  L  R   N  W  Y  N>

1750       1760       1770       1780       1790       1800
          *          *          *          *          *          *
CCCAGTAGCA GGATTACGAC AATCCTTAGA ACAGTATCAA GTTGTAAAAC AACCAGATTA
GGGTCATCGT CCTAATGCTG TTAGGAATCT TGTCATAGTT CAACATTTG TTGGTCTAAT
 P  V  A   G  L  R   Q  S  L  E   Q  Y  Q   V  V  K   Q  P  D  Y>

1810       1820       1830       1840       1850       1860
          *          *          *          *          *          *
CTTACTGGTC CCAGAGGAAG TCATGGAATA TAAACCTAGA AGGAAAAGGG CAGCTATTCA
GAATGACCAG GGTCTCCTTC AGTACCTTAT ATTTGGATCT TCCTTTTCCC GTCGATAAGT
 L  L  V   P  E  E   V  M  E  Y   K  P  R   R  K  R   A  A  I  H>

1870       1880       1890       1900       1910       1920
          *          *          *          *          *          *
TGTTATGTTG GCTCTTGCAA CAGTATTATC TATTGCCGGT GCAGGGACGG GGGCTACTGC
ACAATACAAC CGAGAACGTT GTCATAATAG ATAACGGCCA CGTCCCCTGCC CCCGATGACG
 V  M  L   A  L  A   T  V  L  S   I  A  G   A  G  T   G  A  T  A>
```

FIG. 3I

```
            1930       1940       1950       1960       1970       1980
              *          *          *          *          *          *
       TATAGGGATG GTAACACAAT ACCACCAAGT TCTGGCAACC CATCAAGAAT CTATGAAAA
       ATATCCCTAC CATTGTGTTA TGGTGGTTCA AGACCGTTGG GTAGTTCTTA GATACCTTTT
        I  G  M  V  T  Q   Y  H  Q  V   L  A  T    H  Q  E   S  M  E  K>

1990       2000       2010       2020       2030                SpeI
              *          *          *          *          *
       GGTGACTGAA GCCTTAGAGA TAAACAACTT AAGGTTAGTT ACATTAGAGC ATCAAGTACT
       CCACTGACTT CGGAATCTCT ATTTGTTGAA TTCCAATCAA TGTAATCTCG TAGTTCATGA
        V  T  E   A  L  E   I  N  N  L   R  L  V   T  I  E    H  Q  V  L>

2050       2060       2070       2080       2090       2100
              *          *          *          *          *          *
       AGTAATAGGA TTAAAAGTAG AAGCTATGGA AAAATTTTTA TATACAGCTT TCGCTATGCA
       TCATTATCCT AATTTCATC TTCGATACCT TTTTAAAAAT ATATGTCGAA AGCGATACGT
        V  I  G   L  K  V   E  A  M  E   K  F  L   Y  T  A   F  A  M  Q>

2110       2120       2130       2140       2150       2160
              *          *          *          *          *          *
       AGAATTAGGA TGTAATCCAA ATCAATTTTT CTCCAAAATC CCTCTTGAGT TGTGGACAAG
       TCTTAATCCT ACATTAGGTT TAGTTAAAAA GAGGTTTTAG GGAGAACTCA ACACCTGTTC
        E  L  G   C  N  P   N  Q  F  F   S  K  I   P  L  E   L  W  T  R>
```

FIG. 3J

```
          2170        2180        2190        2200        2210        2220
           *           *           *           *           *           *
        GTATAATATG ACTATAAATC AAACAATATG GAATCATGGA AATATAACTT TGGGGAATG
        CATATTATAC TGATATTTAG TTTGTTATAC CTTAGTACCT TTATATTGAA ACCCCTTAC
         Y  N  M   T  I  N    Q  T  I  W  N  H  G   N  I  T    L  G  E  W>

2230        2240        2250        2260        2270        2280
           *           *           *           *           *           *
        GTATAACCAC ACCAAAGATT TACAACCAAA GTTTTATGAA ATAATAATGG ACATAGAACC
        CATATTGGTG TGGTTTCTAA ATGTTGGTTT CAAAATACTT TATTATTACC TGTATCTTGG
         Y  N  H   T  K  D    L  Q  P  K  F  Y  E   I  I  M    D  I  E  P>

2290        2300        2310        2320        2330        2340
           *           *           *           *           *           *
        AAATAATGTA CAAGGAAAAA CAGGGATACA ACAATTACCC AAGTGGGAAG ATTGGGTAAG
        TTTATTACAT GTTCCCTTTT GTCCCTATGT TGTTAATGGG TTCACCCTTC TAACCCATTC
         N  N  V   Q  G  K    T  G  I  Q  Q  L  P   K  W  E    D  W  V  R>

2350        2360        2370        2380        2390        2400
           *           *           *           *           *           *
        ATGGATAGGA AATATTCCAC AATATTTAAA GGGACTATTG GGAGGTATCT TGGGAATAGG
        TACCTATCCT TTATAGGTG TTATAAATTT CCCTGATAAC CCTCCATAGA ACCCTTATCC
         W  I  G   N  I  P    Q  Y  L  K  G  L  L   G  G  I    L  G  I  G>
```

FIG. 3K

```
        2410       2420       2430       2440       2450       2460
         *          *          *          *          *          *
ATTAGGAGTG TTATTATTGA TTTTATGTTT ACCTACATTG GTTGATTGTA TAAGAAATTG
TAATCCTCAC AATAATAACT AAAATACAAA TGGATGTAAC CAACTAACAT ATTCTTTAAC
 L  G  V   L  L  L    I  L  C  L   P  T  L   V  D  C    I  R  N  C>

2470       2480       2490       2500       2510       2520
         *          *          *          *          *          *
TATCCACAAG ATACTAGGAT ACACAGTAAT TGCAATGCCT GAAGTAGAAG GAGAAGAAAT
ATAGGTGTTC TATGATCCTA TGTGTCATTA ACGTTACGGA CTTCATCTTC CTCTTCTTTA
 I  H  K   I  L  G    Y  T  V  I   A  M  P   E  V  E    G  E  E  I>

2530       2540       2550       2560       2570       2580
         *          *          *          *          *          *
ACAACCACAA ATGGAATTGA GGAGAAATGG TAGCCAATTT GGCATGTCTG AAAAAGAGGA
TGTTGGTGTT TACCTTAACT CCTCTTTACC ATCGGTTAAA CCGTACAGAC TTTTTCTCCT
 Q  P  Q   M  E  L    R  R  N  G   S  Q  F   G  M  S    E  K  E  E>

2590       2600       2610       2620       2630       2640
         *          *          *          *          *          *
GGAATGATGA AGTATCTCAG ACTTATTTTA TAAGGGAGAT ACTGTGCTAA GTTCTTCCCT
CCTTACTACT TCATAGAGTC TGAATAAAAT ATTCCCTCTA TGACACGATT CAAGAAGGGA
 E>
```

FIG. 3L

```
           2650       2660       2670       2680       2690       2700
            *          *          *          *          *          *
TTGAGGAAGG TATGTCATAT GAATCCATTT CGAACCAAAT CAAACTAATA AAGTATGTAT
AACTCCTTCC ATACAGTATA CTTAGGTAAA GCTTGGTTTA GTTTGATTAT TTCATACATA 2710       2720       2730       2740       2750       2760
            *          *          *          *          *          *
TGTAAGGTAA AAGGAAAAGA CAAAGAAGAA GAAGAAAGAA GAAAGCTTTC AAGAGGATGA
ACATTCCATT TTCCTTTTCT GTTTCTTCTT CTTCTTTCTT CTTTCGAAAG TTCTCCTACT 2770       2780       2790       2800       2810       2820
            *          *          *          *          *          *
TGACAGAGTT AGAAGATCGC TTCAGGAAGC TATTTGGCAC GACTTCTACA ACGGGAGACA
ACTGTCTCAA TCTTCTAGCG AAGTCCTTCG ATAAACCGTG CTGAAGATGT TGCCCTCTGT 2830       2840       2850       2860       2870       2880
            *          *          *          *          *          *
GCACAGTAGA TTCTGAAGAT GAACCTCCTA AAAAAGAAAA AAGGGGTGGAC TGGGATGAGT
CGTGTCATCT AAGACTTCTA CTTGGAGGAT TTTTTCTTTT TTCCCACCTG ACCCTACTCA 2890       2900       2910       2920       2930       2940
            *          *          *          *          *          *
ATTGGAACCC TGAAGAAATA GAAAGAATGC TTATGGACTA GGGACTGTTT ACGAACAAAT
TAACCTTGGG ACTTCTTTAT CTTTCTTACG AATACCTGAT CCCTGACAAA TGCTTGTTTA
```

FIG. 3M

```
          2950       2960       2970       2980       2990       3000
           *          *          *          *          *          *
GATAAAGGA AATAGCTAAG CATGACTCAT AGTTAAAGCG CTAGCAGCTG CTTAACCGCA
CTATTTCCT TTATCGATTC GTACTGAGTA TCAATTTCGC GATCGTCGAC GAATTGGCGT 3010       3020       3030       3040       3050       3060
           *          *          *          *          *          *
AAACCACATC CTATGTAAAG CTTGCTAATG ACGTATAAGT TGTTCCATTG TAAGAGTATA
TTTGGTGTAG GATACATTTC GAACGATTAC TGCATATTCA ACAAGGTAAC ATTCTCATAT 3070       3080       3090       3100       3110       3120
           *          *          *          *          *          *
TAACCAGTGC TTTGTGAAAC TTCGAGGAGT CTCTCCGTTG AGGACTTTCG AGTTCTCCCT
ATTGGTCACG AAACACTTTG AAGCTCCTCA GAGAGGCAAC TCCTGAAAGC TCAAGAGGA 3130       3140       3150       3160       3170       3180
           *          *          *          *          *          *
ACAGATACAA TAAATATTTG AGATTGAACC CTGTCAAGTA TCTGTGTAAT
TGTCTATGTT ATTTATAAAC TCTAACTTGG GACAGTTCAT AGACACATTA 3190       3200       3210       3220
           *          *          *          *
TGAGGCTCCC ACACCCGAGG CGGAATCCGG GCCGAGAACT TCGCA
ACTCCGAGGG TGTCTATGTT GCCTTAGGCC CGGCTCTTGA AGCGT

CTTTTTTACC
GAAAAAATGG
```

FIG. 5A

```
         10         20         30         40         50         60
          *          *          *          *          *          *
ATGGGAATG GACAGGGGCG AGATTGGAAA ATGGCCATTA AGAGATGTAG TAATGCTGCT
TACCCTTAC CTGTCCCCGC TCTAACCTTT TACCGGTAAT TCTCTACATC ATTACGACGA
 M  G  N   G  Q  G  R   D  W  K   M  A  I   K  R  C  S   N  A  A>

---> p15 Matrix protein 70         80         90        100        110        120
          *          *          *          *          *          *
GTAGGAGTAG GGGGGAAGAG TAAAAAATTT GGGGAAGGGA ATTTCAGATG GGCCATTAGA
CATCCTCATC CCCCCTTCTC ATTTTTTAAA CCCCTTCCCT TAAAGTCTAC CCGGTAATCT
 V  G  G   G  G  K  S   K  K  F   G  E  G   N  F  R  W   A  I  R>

130        140        150        160        170        180
          *          *          *          *          *          *
ATGGCTAATG TATCTACAGG ACGAGAACCT GGTGATATAC CAGAGACTTT AGATCAACTA
TACCGATTAC ATAGATGTCC TGCTCTTGGA CCACTATATG GTCTCTGAAA TCTAGTTGAT
 M  A  N   V  S  T  G   R  E  P   G  D  I   P  E  T  L   D  Q  L>
```

FIG. 5B

```
        190        200        210        220        230        240
         *          *          *          *          *          *
AGGTTGGTTA TTTGCGATTT ACAAGAAAGA AGAAAAAAT  TTGGATCTTG CAAAGAAATT
TCCAACCAAT AAACGCTAAA TGTTCTTTCT TCTTTTTTA  AACCTAGAAC GTTTCTTTAA
 R  L  V   I  C  D  L   Q  E  R   R  K  K    F  G  S  C  K  E  I>

250        260        270        280        290        300
         *          *          *          *          *          *
GATAAGGCAA TTGTTACATT AAAAGTCTTT GCGGCAGTAG GACTTTTAAA TATGACAGTG
CTATTCCGTT AACAATGTAA TTTTCAGAAA CGCCGTCATC CTGAAAATTT ATACTGTCAC
 D  K  A   I  V  T  L   K  V  F   A  A  V    G  L  N   M  T  V>

310        320        330        340        350        360
         *          *          *          *          *          *
TCTTCTGCTG CTGCAGCTGA AAATATGTTC ACTCAGATGG GATTAGACAC TAGACCATCT
AGAAGACGAC GACGTCGACT TTTATACAAG TGAGTCTACC CTAATCTGTG ATCTGGTAGA
 S  S  A   A  A  A  E   N  M  F   T  Q  M    G  L  D  T  R  P  S>

370        380        390        400        410        420
         *          *          *          *          *          *
ATGAAAGAAG CAGGAGGAAA AGAGGAAGGC CCTCCACAGG CATTTCCTAT TCAAACAGTA
TACTTTCTTC GTCCTCCTTT TCTCCTTCCG GGAGGTGTCC GTAAAGGATA AGTTTGTCAT
 M  K  E   A  G  G  K   E  E  G   P  P  Q    A  F  P  I  Q  T  V>
```

FIG. 5C p15 <------   ------> p25
               Capsid protein

```
         430        440        450        460        470        480
          *          *          *          *          *          *
AATGGAGTAC CACAATATGT AGCACTTGAC CCAAAAATGG TGTCCATTTT TATGGAAAAG
TTACCTCATG GTGTTATACA TCGTGAACTG GGTTTTTACC ACAGGTAAAA ATACCTTTTC
 N  G  V  P  Q  Y  V  A  L  D  P  K  M  V  S  I  F  M  E  K>

490        500        510        520        530        540
          *          *          *          *          *          *
GCAAGAGAAG GATTAGGAGG TGAGGAAGTT CAGCTATGGT TCACTGCCTT CTCTGCAAAT
CGTTCTCTTC CTAATCCTCC ACTCCTTCAA GTCGATACCA AGTGACGGAA GAGACGTTTA
 A  R  E  G  L  G  G  E  E  V  Q  L  W  F  T  A  F  S  A  N>

550        560        570        580        590        600
          *          *          *          *          *          *
TTAACACCTA CTGACATGGC CACATTAATA ATGGCCGCAC CAGGGTGCGC TGCAGATAAA
AATTGTGGAT GACTGTACCG GTGTAATTAT TACCGGCGTG GTCCCACGCG ACGTCTATTT
 L  T  P  T  D  M  A  T  L  I  M  A  A  P  G  C  A  A  D  K>
```

FIG. 5D

```
        610        620        630        640        650        660
         *          *          *          *          *          *
GAAATATTGG ATGAAAAGCTT AAAGCAACTT ACTGCAGGAT ATGATCGTAC ACATCCCCCT
CTTTATAACC TACTTTCGAA TTTCGTTGAA TGACGTCCTA TACTAGCATG TGTAGGGGA
 E  I  L  D  E  S  L  K  Q  L  T  A  G  Y  D  R  T  H  P  P>
                                           M  I  V  H  I  P  L>

670        680        690        700        710        720
         *          *          *          *          *          *
GATGCTCCCA GACCATTACC CTATTTTACT GCAGCAGAAA TTATGGGTAT TGGATTACT
CTACGAGGGT CTGGTAATGG GATAAAATGA CGTCGTCTTT AATACCCATA ACCTAAATGA
 D  A  P  R  P  L  P  Y  F  T  A  A  E  I  M  G  I  G  F  T>
 M  L  P  D  H  Y  P  I  L  L  Q  Q  K  L  W  V  L  D  L  L>

730        740        750        760        770        780
         *          *          *          *          *          *
CAAGAACAAC AAGCAGAAGC AAGATTTGCA CCAGCTAGGA TGCAGTGTAG AGCATGGTAT
GTTCTTGTTG TTCGTCTTCG TTCTAAACGT GGTCGATCCT ACGTCACATC TCGTACCATA
 Q  E  Q  Q  A  E  A  R  F  A  P  A  R  M  Q  C  R  A  W  Y>
 K  N  N  K  Q  K  Q  D  L  H  Q  L  G  C  S  V  E  H  G  I>
```

FIG. 5E

```
       790        800        810        820        830        840
        *          *          *          *          *          *
CTCGAGGGAC TAGGAAAATT GGGCGCCATA AAAGCTAAGT CTCCTCGAGC TGTGCAGTTA
GAGCTCCCTG ATCCTTTTAA CCCGCGGTAT TTTCGATTCA GAGGAGCTCG ACACGTCAAT
 L  E  G   L  G  K  L   G  A  I   K  A  K    S  P  R  A   V  Q  L >
 S  R  D >

850        860        870        880        890        900
        *          *          *          *          *          *
AGACAAGGAG CTAAGGAAGA TTATTCATCC TTTATTGACA GATTGTTTGC CCAAATAGAT
TCTGTTCCTC GATTCCTTCT AATAAGTAGG AAATAACTGT CTAACAAACG GGTTTATCTA
 R  Q  G   A  K  E  D   Y  S  S   F  I  D    R  L  F  A   Q  I  D >

910        920        930        940        950        960
        *          *          *          *          *          *
CAAGAACAAA ATACAGCTGA AGTTAAGTTA TATTAAAAAC AGTCATTAAG CATGGCTAAT
GTTCTTGTTT TATGTCGACT TCAATTCAAT ATAAATTTTG TCAGTAATTC GTACCGATTA
 Q  E  Q   N  T  A  E   V  K  L   Y  L  K    Q  S  L  S   M  A  N >

970        980        990       1000       1010       1020
        *          *          *          *          *          *
GCTAATGCAG AATGTAAAAA GCCAATGACC CAGAAAGTAC CCTAGAAGAA GTCTTTCTT
CGATTACGTC TTACATTTTT CGGTTACTGG GTCTTTCATG GGATCTTCTT CAGAAAGAA
 A  N  A   E  C  K  K   P  M  T   H  L  K    P  E  S  T   L  E  E >
```

FIG. 5F

```
       1030       1040       1050       1060       1070       1080
          *          *          *          *          *          *
AAGTTGAGAG CTTGTCAAGA AATAGGCTCA CCAGGATATA AAATGCAACT CTTGGCAGAA
TTCAACTCTC GAACAGTTCT TTATCCGAGT GGTCCTATAT TTTACGTTGA GAACCGTCTT
 K  L  R   A  C  Q  E   I  G  S   P  G  Y   K  M  Q   L  A  E > p25 <----  -----> p10
                                                      Nucleocapsid 1090       1100       1110       1120       1130       1140
          *          *          *          *          *          *
GCTCTTACAA AAGTTCAAGT AGTGCAATCA AAAGGATCAG GACCAGTGTG TTTTAATTGT
CGAGAATGTT TTCAAGTTCA TCACGTTAGT TTTCCTAGTC CTGGTCACAC AAAATTAACA
 A  L  T   K  V  Q  V   V  Q  S   K  G  S   G  P  V  C   F  N  C 1150       1160       1170       1180       1190       1200
          *          *          *          *          *          *
AAAAAACCAG GACATCTAGC AAGACAATGT AGAGAAGTGA GAAAATGTAA TAAATGTGGA
TTTTTTGGTC CTGTAGATCG TTCTGTTACA TCTCTTCACT CTTTTACATT ATTTACACCT
 K  K  P   G  H  L  A   R  Q  C   K  D  N  V   R  E  V   R  K  C   N  K  C  G >
```

FIG. 5G

```
     1210       1220       1230       1240       1250       1260
      *          *          *          *          *          *
AAACCTGGTC ATGTAGCTGC CAAATGTTGG CAAGGAAATA GAAAGAATTC GGGAAACTGG
TTTGGACCAG TACATCGACG GTTTACAACC GTTCCTTTAT CTTTCTTAAG CCCTTTGACC
 K  P  G   H  V  A  A   K  C  W    Q  G  N    R  K  N  S   G  N  W>

1270       1280       1290       1300       1310       1320
      *          *          *          *          *          *
AAGGCGGGGC GAGCTGCAGC CCCAGTGAAT CAAGTGCAGC AAGCAGTAAT GCCATCTGCA
TTCCGCCCCG CTCGACGTCG GGGTCACTTA GTTCACGTCG TTCGTCATTA CGGTAGACGT
 K  A  G    R  A  A    P  V  N    Q  V  Q    Q  A  V  M   P  S  A>

1330       1340       1350
      *          *          *
CCTCCAATGG AGGAGAAACT ATTGGATTTA TAA
GGAGGTTACC TCCTCTTTGA TAACCTAAAT ATT
 P  P  M   E  E  K  L   L  D  L> p10 ----->
```

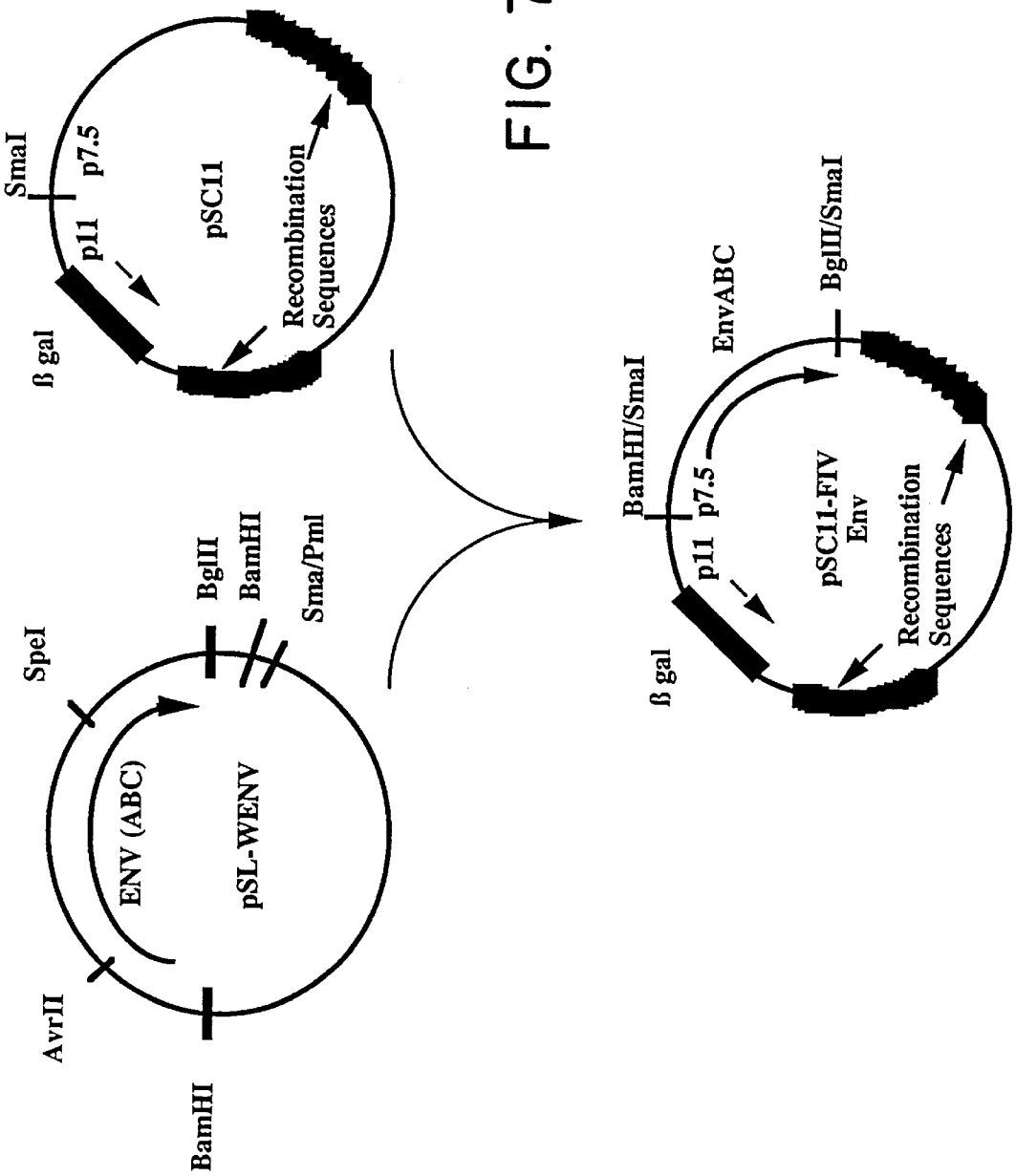

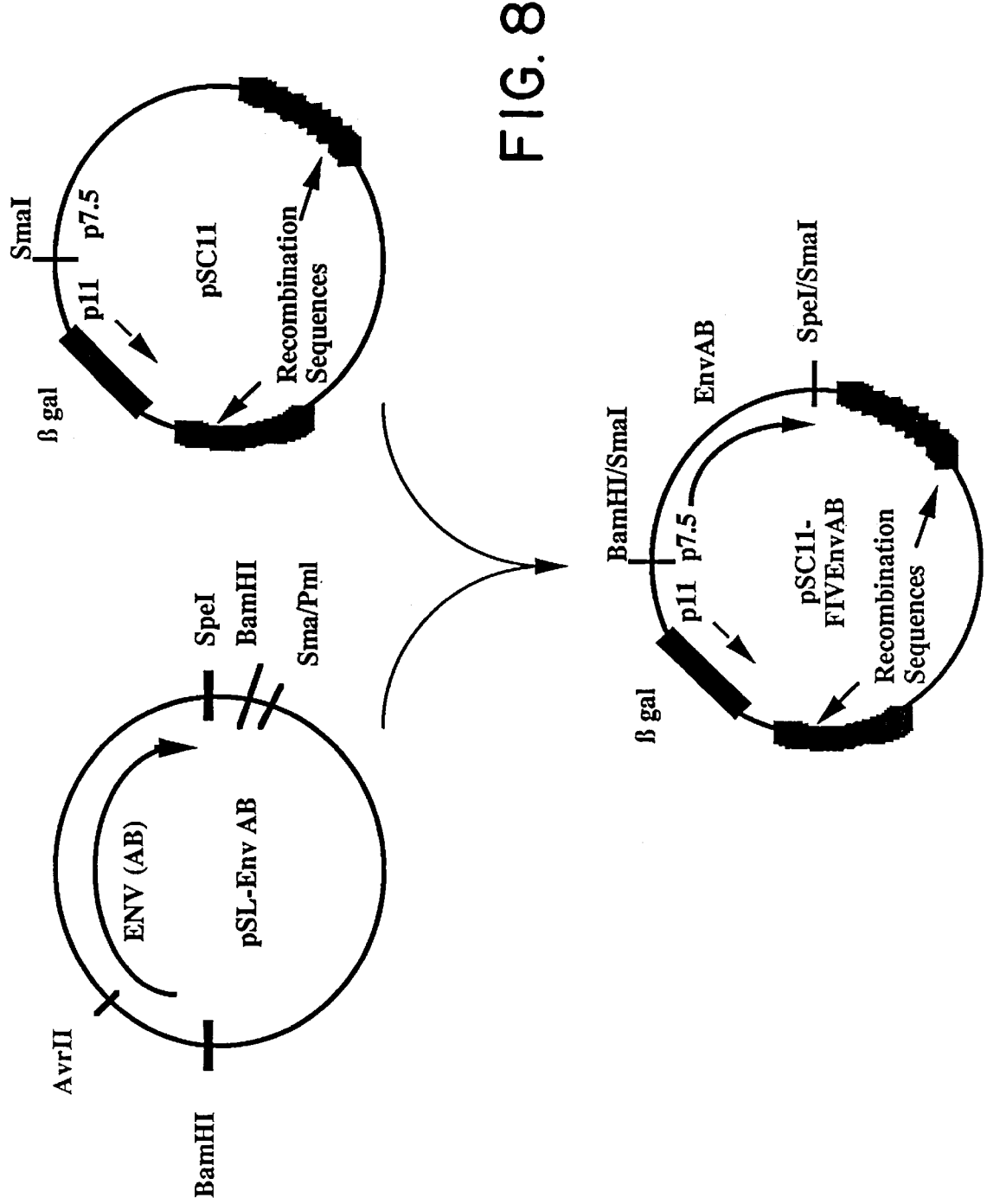

| Cat ID | Vaccination Route | Pre Challenge Viremia * | Pre Challenge CD4:CD8 | 1 Month Post Challenge Viremia * | 1 Month Post Challenge CD4:CD8 | 3 Months Post Challenge Viremia * | 3 Months Post Challenge CD4:CD8 | 9 Months Post Challenge Viremia * | 9 Months Post Challenge CD4:CD8 |
|---|---|---|---|---|---|---|---|---|---|
| RCNV-FIV gag Vaccinates | | | | | | | | | |
| AQC3 | SC | NEG | 2.70 | NEG | 1.82 | POS | 0.30 | NA | 0.61 |
| AQD4 | SC | NEG | 3.62 | NEG | 1.71 | POS | 2.18 | POS | 1.18 |
| ATF1 | SC | NEG | 3.80 | NEG | 3.87 | POS | 1.08 | POS | 1.12 |
| ATH3 | SC | NEG | 1.93 | NEG | 3.26 | POS | 0.40 | DEAD | 0.94 |
| ATI1 | SC | NEG | 3.23 | NEG | 2.17 | POS | 1.12 | POS | 0.86 |
| AQE4 | IM | NEG | 3.37 | NEG | 2.95 | POS | 1.24 | NEG | 1.19 |
| AQT4 | IM | NEG | 1.59 | NEG | 3.68 | POS | 1.44 | NA | 0.79 |
| AQY4 | IM | NEG | 2.41 | NEG | 3.86 | POS | 0.64 | POS | 0.77 |
| ATI2 | IM | NEG | 3.63 | NEG | 3.28 | POS | 1.49 | POS | 1.67 |
| ATJ1 | IM | NEG | 3.27 | NEG | 3.73 | POS | 1.05 | POS | 1.11 |
| RCNV-FIV envAB Vaccinates | | | | | | | | | |
| ARB4 | SC | NEG | 2.72 | NEG | 2.12 | NEG | 2.27 | NEG | 1.65 |
| ARO2 | SC | NEG | 3.20 | NEG | 2.26 | POS | 0.67 | POS | 1.18 |
| ATJ4 | SC | NEG | 2.16 | NEG | 2.54 | POS | 0.60 | POS | 0.76 |
| ATK1 | SC | NEG | 3.06 | NEG | 2.27 | POS | 0.90 | POS | 0.74 |
| ATL1 | SC | NEG | 2.32 | POS | 3.46 | POS | 1.16 | POS | 1.44 |
| ARD4 | IM | NEG | 3.04 | POS | 2.29 | POS | 1.07 | POS | 1.04 |
| ARE4 | IM | NEG | 2.20 | POS | 2.89 | POS | 1.23 | POS | 1.00 |
| ARG4 | IM | NEG | 2.48 | NEG | 2.79 | POS | 1.25 | NA | 1.02 |
| ATL2 | IM | NEG | 3.44 | POS | 2.63 | POS | 1.16 | POS | 1.04 |
| ATL3 | IM | NEG | 2.44 | NEG | 3.14 | POS | 1.30 | POS | 1.06 |

RCNV-FIV envAB + RCNV-FIV gag Vaccinates

| | | | | | | | | | |
|---|---|---|---|---|---|---|---|---|---|
| ARN4 | SC | NEG | 3.04 | NEG | 2.73 | NEG | 1.88 | POS | 1.11 |
| AR02 | SC | NEG | 3.14 | POS | 3.09 | POS | 0.41 | POS | 0.51 |
| AR03 | SC | NEG | 2.76 | NEG | 4.11 | POS | 0.77 | POS | 0.74 |
| ATL4 | SC | NEG | 2.55 | NEG | 3.43 | NEG | 0.80 | POS | 0.88 |
| ATM1 | SC | NEG | 3.78 | NEG | 2.57 | POS | 0.67 | POS | 0.81 |

Wild Type RCNV Vaccinates (Controls)

| | | | | | | | | | |
|---|---|---|---|---|---|---|---|---|---|
| ARQ4 | SC | NEG | 2.87 | NEG | 2.54 | NEG | 0.55 | POS | 0.86 |
| ARR4 | SC | NEG | 2.29 | POS | 1.93 | POS | 0.77 | POS | 0.70 |
| ATM2 | SC | NEG | 2.64 | NEG | 1.69 | POS | 0.92 | POS | 0.93 |
| ATM3 | SC | NEG | 3.91 | POS | 2.90 | POS | 0.62 | POS | 0.78 |
| ATN1 | SC | NEG | 3.01 | POS | 3.62 | POS | 1.09 | POS | 0.99 |

SC = Subcutaneous Vaccination
IM = Intramuscular Vaccination

NA = Not Available due to Contaminated Culture
*Viremia Detected by Culture Isolation of FIV from Peripheral Blood Mononuclear Cells
CD4:CD8 = Ratio of CD4 Positive Lymphocytes to CD8 Positive Lymphocytes as Measured by Flow Cytometry

FIG. 10

| Time Point After Challenge | Group | % of Cats Viremic | Preventable Fraction✱ | % of Cats CD4:CD8 <1.0 | Preventable Fraction✱ |
|---|---|---|---|---|---|
| 1 Months | Controls | 60% |  | 0% |  |
|  | RCNV-FIV gag | 0% | 100% | 0% | NA |
|  | RCNV-FIV envAB | 40% | 33% | 0% | NA |
|  | RCNV-FIV gag + envAB | 20% | 67% | 0% | NA |
| 3 Months | Controls | 80% |  | 80% |  |
|  | RCNV-FIV gag | 100% | 0% | 30% | 63% |
|  | RCNV-FIV envAB | 90% | 0% | 30% | 63% |
|  | RCNV-FIV gag + envAB | 60% | 25% | 40% | 50% |
| 9 Months | Controls | 100% |  | 100% |  |
|  | RCNV-FIV gag | 86% | 14% | 50% | 50% |
|  | RCNV-FIV envAB | 89% | 11% | 20% | 80% |
|  | RCNV-FIV gag + envAB | 100% | 0% | 80% | 20% |

✱Preventable Fraction = [(% Controls with Sign) − (% Vaccinates with Sign)] ÷ (% Controls with Sign) × 100

FIG. IIA

| Cat ID | Vaccination Route | Depression | Ocular Discharge | Nasal Discharge | Dyspnea | Fever | Total Score |
|---|---|---|---|---|---|---|---|
| RCNV-FIV Gag Vaccinates | | | | | | | |
| AQC3 | SC | 0 | 0 | 0 | 0 | 8 | 8 |
| AQD4 | SC | 1 | 0 | 0 | 0 | 5 | 6 |
| ATF1 | SC | 0 | 0 | 0 | 0 | 2 | 2 |
| ATH3 | SC | DEAD | DEAD | DEAD | DEAD | DEAD | DEAD |
| ATI1 | SC | 0 | 0 | 1 | 8 | 4 | 13 |
| AQE4 | IM | 0 | 1 | 1 | 28 | 5 | 35 |
| AQT4 | IM | 0 | 1 | 2 | 0 | 2 | 5 |
| AQY4 | IM | 0 | 0 | 0 | 0 | 7 | 7 |
| ATI2 | IM | 0 | 1 | 0 | 0 | 3 | 4 |
| ATJ1 | IM | 0 | 0 | 0 | 0 | 3 | 3 |
| | Average | 0.1 | 0.3 | 0.4 | 4.0 | 4.3 | 9.2 |
| | %Reduction | 0% | 86% | 0% | 55% | 0% | 41% |

FIG. IIB

| RCNV-FIV envAB Vaccinates | | | | | | | |
|---|---|---|---|---|---|---|---|
| ARB4 | SC | 0 | 0 | 0 | 0 | 15 | 15 |
| ARO2 | SC | 0 | 0 | 1 | 4 | 1 | 6 |
| ATJ4 | SC | 0 | 1 | 0 | 4 | 5 | 9 |
| ATK1 | SC | 0 | 0 | 0 | 0 | 7 | 8 |
| ATL1 | SC | 0 | 0 | 0 | 4 | 0 | 4 |
| ARD4 | IM | 0 | 0 | 0 | 0 | 1 | 1 |
| ARE4 | IM | 0 | 0 | 0 | 0 | 0 | 1 |
| ARG4 | IM | 0 | 0 | 0 | 12 | 9 | 12 |
| ATL2 | IM | 0 | 0 | 0 | 0 | 0 | 9 |
| ATL3 | IM | 0 | 1 | 0 | 0 | 0 | 1 |
| Average | | 0.0 | 0.2 | 0.1 | 2.4 | 3.9 | 6.6 |
| %Reduction | | 0% | 92% | 75% | 73% | 3% | 58% |

| Wild Type RCNV Vaccinates (Controls) | | | | | | | |
|---|---|---|---|---|---|---|---|
| ARQ4 | SC | 0 | 2 | 0 | 0 | 0 | 2 |
| ARR4 | SC | 0 | 0 | 0 | 0 | 12 | 12 |
| ATM2 | SC | 0 | 1 | 1 | 12 | 0 | 14 |
| ATM3 | SC | 0 | 9 | 1 | 32 | 7 | 49 |
| ATN1 | SC | 0 | 0 | 0 | 0 | 1 | 1 |
| Average | | 0.0 | 2.4 | 0.4 | 8.8 | 4.0 | 15.6 |

RECOMBINANT RACCOON POX VIRUSES AND THEIR USE AS AN EFFECTIVE VACCINE AGAINST FELINE IMMUNODEFICIENCY VIRUS INFECTION

This application is a divisional of application Ser. No. 08/482,090, filed Jun. 7, 1995 now U.S. Pat. No. 5,820,369, issued Oct. 13, 1998, which is incorporated herein by reference in its entirety.

FIELD OF THE INVENTION

The present invention pertains to the prophylaxis of disease caused by feline immunodeficiency virus (FIV), using as vaccines recombinant raccoon poxviruses (RRPVs) expressing the gag and envelope proteins of FIV.

BACKGROUND OF THE INVENTION

Feline immunodeficiency virus (FIV) infection is a significant health problem for domestic cats around the world. As in its human counterpart, infection with FIV causes a progressive disruption in immune function. In the acute phase of infection, the virus causes transient illness associated with symptoms such as lymphadenopathy, pyrexia, and neutropenia. Subsequently, an infected animal enters an asymptomatic phase of 1–2 years before clinical manifestations of immune deficiency become apparent, after which the mean survival time is usually less than one year.

FIV is a typical retrovirus that contains a single-stranded polyadenylated RNA genome, internal structural proteins derived from the gag gene product, and a lipid envelope containing membrane proteins derived from the env gene product (Bendinelli et al., *Clin.Microbiol.Rev.* 8:87, 1995). The gag gene is translated into a primary product of about 50 kDa that is subsequently cleaved by a viral protease into the matrix, capsid, and nucleocapsid proteins. The env gene yields a primary translation product of 75–80 kDa (unglycosylated molecular weight); in infected cells, the precursor has an apparent molecular weight of 145–150 kDa due to N-linked glycosylation. The env precursor is cleaved in the Golgi apparatus into the SU and TM proteins (also designated gp95 and gp40, respectively).

Most vaccines against FIV have failed to induce protective immunity. Ineffective vaccines have involved inactivated whole virus, fixed infected cells, recombinant CA and SU proteins, and a synthetic peptide corresponding to the V3 region of SU. In some cases, the vaccine actually enhanced infection after challenge. In one system, vaccination with paraformaldehyde-fixed virus or infected cells resulted in protective immunity (Yamamoto et al., *J. Virol.* 67:601, 1993), but application of this approach by others was unsuccessful (Hosie et al., in *Abstracts of the International Symposium on Feline Retrovirus Research*, 1993, page 50).

Thus, there is a need in the art for an effective vaccine against FIV that utilizes the gag or env proteins, or fragments therefrom, as immunogens.

SUMMARY OF THE INVENTION

The present invention pertains to the prevention or lessening of disease in cats caused by Feline Immunodeficiency Virus (FIV). Prevention or lessening of disease is understood to mean the amelioration of any symptoms, including immune system disruptions, that result from FIV infection.

The invention provides recombinant raccoon poxviruses having at least one internal gene comprising a DNA sequence that encodes FIV gag protein (gag), FIV envelope protein (env), a polypeptide consisting of amino acids 1–735 of FIV env, or immunogenic fragments of any of the foregoing. By immunogenic fragment is meant any portion of the coding sequence of FIV gag or env polypeptides that induces a beneficial immune response in cats.

In another aspect, the invention encompasses vaccines that comprise one or more of the FIV-expressing recombinant raccoon poxviruses described above, with a pharmaceutically acceptable carrier or diluent and a pharmaceutically acceptable adjuvant.

In yet another aspect, the invention provides methods for preventing or lessening disease caused by FIV, which is carried out by administering to a feline in need of such treatment the vaccines described above.

BRIEF DESCRIPTION OF THE DRAWINGS

FIGS. 3A–3M show the DNA [SEQ. I.D. NO. 16] and protein [SEQ. I.D. NO. 14] sequence of the env gene of FIV.

FIGS. 5A–5G show the DNA [SEQ. I.D. NO. 15] and protein [SEQ. I.D. NO. 13] sequence of the gag gene of FIV.

FIG. 7 is a graphic illustration of the cloning strategy for construction of the raccoon poxvirus transfer plasmid pSC11-FIV Env.

FIG. 8 is a graphic illustration of the cloning strategy for construction of the raccoon poxvirus transfer plasmid pSC11-FIV EnvAB.

FIGS. 9A and 9B are a table illustrating the detection of viremia and CD4:CD8 ratios in vaccinated and unvaccinated cats after FIV challenge.

FIG. 10 is a table illustrating the preventable fraction for viremia and CD4:CD8 ratio changes in vaccinated and unvaccinated cats following FIV challenge.

FIGS. 11A and 11B are a table illustrating the clinical scores of vaccinated and unvaccinated cats after challenge with *Toxoplasma gondii*.

DETAILED DESCRIPTION OF THE INVENTION

Figure 1A:
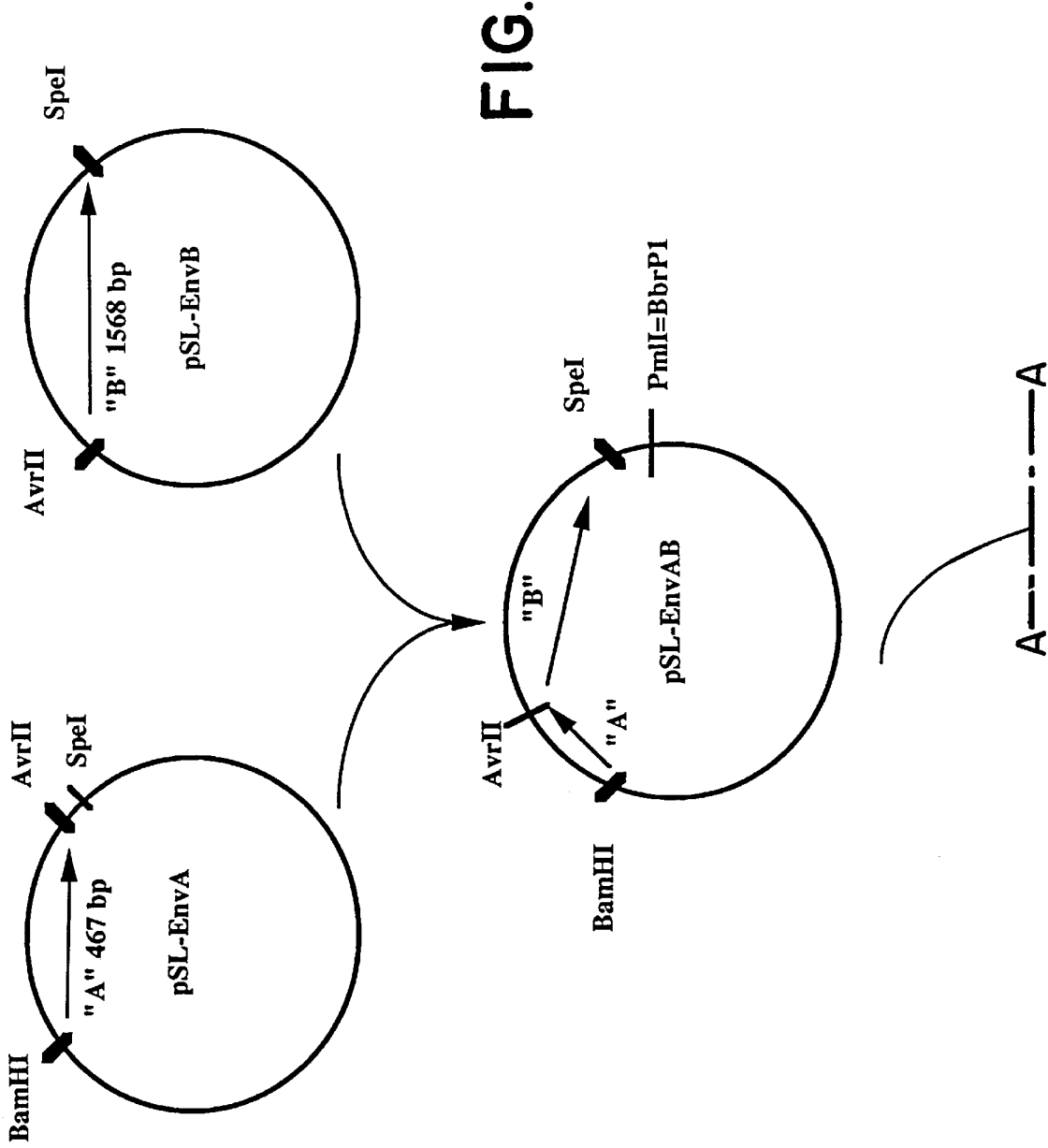
FIGS. 1A and 1B is a graphic illustration of the cloning strategy for the envelope gene of FIV.

All patents, patent applications, and references cited herein are hereby incorporated by reference in their entirety. In the case of inconsistencies, the present disclosure, including definitions, will control.

The vaccine of the present invention may be prepared by creating recombinant raccoon poxviruses (RRPVs) containing a gene encoding the gag or env proteins of Feline Immunodeficiency Virus (FIV) or immunogenic fragments thereof. Gag and env genes useful in practicing the present invention may be obtained by methods well-known in the art. In one embodiment, viral RNA is reverse-transcribed using endogenous or exogenous reverse transcriptase and the DNA is rendered double-stranded using DNA polymerase. The gag and env-encoding DNA segments are then recovered by restriction enzyme digestion and are amplified by cloning in *E. coli*. In another embodiment, FIV-infected cat cells serve as a source of FIV proviral DNA. In this embodiment, chromosomal DNA is isolated from the cells, and oligonucleotide primers are used to specifically amplify the gag and env genes or fragments therefrom using polymerase chain reaction techniques. This approach is broadly applicable to purifying gag and env genes from different FIV strains or isolates, since primers can be designed from non-polymorphic regions of the FIV genome.

FIV gag and env genes isolated by the above methods are first inserted into a transfer plasmid, and the recombinant plasmid is introduced into appropriate host cells that have been previously infected with a raccoon poxvirus. As a result, the DNA from the transfer plasmid is incorporated into the poxvirus DNA by homologous recombination, producing the RRPVs that are released from the cells.

DNA encoding the FIV gag or env proteins or fragments therefrom are inserted into a transfer plasmid downstream of a poxvirus promoter. In a preferred embodiment, the early/late 7.5 kD protein promoter of vaccinia virus is used. However, alternate promoter elements could be used.

The preferred transfer plasmid also contains a beta-galactosidase marker gene, which allows for selection and detection of the plasmid DNA sequences in recombinant viruses. It will be understood by those of ordinary skill in the art that alternate selectable marker genes, such as the neomycin resistance gene or the *E. coli* gpt gene or others, could be used to practice the invention. Flanking the inserted FIV gene and the selectable marker gene are thymidine kinase DNA sequences, which facilitate integration of the plasmid DNA sequences into the raccoon poxvirus DNA by homologous recombination.

Recombinant viruses expressing the FIV gag or env genes are prepared by first infecting a susceptible cell line (such as Vero [ATCC CCL 81], BSC-1 [ATCC CCL 26], RAT-2 [ATCC CRL 1764], or CRFK [ATCC CCL 94]) with wild type raccoon poxvirus (ATCC VR-838 or similar isolates). Transfer plasmid DNA containing the FIV gag or env gene is then transfected into the infected cells using cationic liposome-mediated transfection, or other suitable techniques such as electroporation or calcium-phosphate precipitation. Raccoon poxviruses incorporate DNA from the transfer plasmid through homologous recombination with the thymidine kinase gene sequences present on the plasmid. Virus infection is allowed to proceed until cytopathic effects are noted in all cells.

Incorporation of the FIV gag or env gene into poxvirus DNA is accompanied by disruption of the viral thymidine kinase gene. Thus, recombinant virus may be selected for by the absence of a thymidine kinase gene; this is achieved by selective expansion on RAT-2 cells (tk-, ATCC CRL 1764) in the presence of 5-bromodeoxyuridine. Viruses containing a gene insert from the transfer plasmid are identified by blue plaque color when grown in the presence of a chromogenic substrate for beta-galactosidase such as X-gal.

Viral plaques that survive these selection and screening procedures are then subjected to several cycles of plaque purification. Subsequently, the presence of the gag or env genes is confirmed by polymerase chain reaction technology, and the presence of gag or env antigenic determinant is confirmed by immunoblot analysis using specific antibodies. These viruses are designated by RRPV-FIV gag and RRPV-FIV env, respectively.

In a further embodiment of the present invention, RRPVs can be produced that express less-than-full-length segments of the FIV gag and env proteins. The techniques used to engineer transfer plasmids encoding partial sequences of env and gag are well-known and widely used in the art, as are the methods for production and screening of RRPVs as detailed in this specification. For example, convenient restriction enzyme recognition sites can be used to obtain fragments of either gene, as described, e.g., Example 1 below. Alternatively, introduction of oligonucleotides containing a stop codon at various points along gag or env DNA will produce a nested set of carboxyterminal-truncated versions of that gene, which can then be incorporated into RRPVs. Furthermore, sequences that encode different domains on each protein may be recombined, using domains derived from different FIV strains or isolates. It will be apparent to one of ordinary skill in the art that systematic screening of such recombinant RRPVs can establish whether the intact protein, subfragments thereof or multi-strain recombinants thereof, are most preferred in practicing the present invention. Furthermore, as stated above, DNA encoding different fragments of gag and env can be used in a combination vaccine after incorporation into the same, or different, RRPVs.

For vaccine preparation, susceptible cells are grown in minimum essential media containing fetal bovine serum or a suitable media substitute. Cells are infected with recombinant raccoon poxvirus at a multiplicity of infection of 0.1 infectious units/cell or less. In this specification an infectious unit is defined as a Tissue Culture Infectious Dose ($TCID_{50}$), an amount of virus yielding 50% infection under defined conditions. When cytopathology is noted in >90% of the cells, the infected cells and extracellular fluids are harvested. The virus may be stored frozen (−50° C. or colder) or lyophilized until the time of use. Compounds such as NZ-amine, dextrose, gelatin or others designed to stabilize the virus during freezing and lyophilization may be added. The virus may be concentrated using commercially available equipment.

Typically, the concentration of virus in the vaccine formulation will be a minimum of $10^{6.5}$ $TCID_{50}$ per dose, but will typically be in the range of $10^{7.0}$ to $10^{9.0}$ $TCID_{50}$ per dose. At the time of vaccination, the virus is thawed (if frozen) or reconstituted (if lyophilized) with a physiologically-acceptable carrier such as deionized water, saline, phosphate buffered saline, or the like.

In one embodiment, a physiologically acceptable adjuvant such as, for example, EMA31, Adjuvant A, or combinations thereof, is added to the vaccine formulation. Non-limiting examples of suitable adjuvants include squalane and squalene (or other oils of animal origin); block copolymers such as Pluronic® (L121) Saponin; detergents such as Tween®-80; Quil® A, mineral oils such as Drakeol® or Marcol®, vegetable oils such as peanut oil; Corynebacterium-derived adjuvants such as *corynebacterium parvum*;Propionibacterium-derived adjuvants such as *Propionibacterium acne; Mycobacterium bovis* (Bacillus Calmette and Guerinn, or BCG); interleukins such as interleukin 2 and interleukin-12; monokines such as interleukin 1; tumor necrosis factor; interferons such as gamma interferon; combinations such as saponin-aluminum hydroxide or Quil®-A aluminum hydroxide; liposomes; iscom adjuvant; mycobacterial cell wall extract; synthetic glycopeptides such as muramyl dipeptides or other derivatives; Avridine; Lipid A; dextran sulfate; DEAE-Dextran or DEAE-Dextran with aluminum phosphate; carboxypolymethylene, such as Carbopol®; EMA; acrylic copolymer emulsions such as Neocryl® A640 (e.g. U.S. Pat. No. 5,047,238); vaccinia or animal poxvirus proteins; subviral particle adjuvants such as orbivirus; cholera toxin; dimethyldiocledecylammonium bromide; or mixtures thereof.

EMA 31 (Monsanto, St. Louis, Mo.) is a linear ethylene/maleic copolymer with approximately equal amounts of ethylene and maleic anhydride, having an estimated average molecular weight of about 75,000 to 100,000. Adjuvant A is an adjuvant comprising a block copolymer, such as a polyoxypropylene-polyoxyethylene (POP-POE) block copolymer, preferably Pluronic® L121 (e.g. U.S. Pat. No. 4,772,466), and an organic component, such as a metabolizable oil, e.g. an unsaturated turpin hydrocarbon, preferably squalane (2,6,10,15,19,23-hexamethyltetracosane) or squalene. The vaccine may also include a non-ionic detergent or surfactant, preferably a polyoxyethylene sorbitan monooleate such as a Tween® detergent, most preferably Tween®-80, i.e. polyoxyethylene (20) sorbitan monooleate.

In this adjuvant mixture, the block copolymer, organic oil, and surfactant may be present in amounts ranging from about 10 to about 40 ml/L, about 20 to about 80 ml/L, and about 1.5 to about 6.5 ml/L, respectively. In a preferred embodiment of the stock adjuvant, the organic component is squalane present in an amount of about 40 mL/L, the surfactant is polyoxyethylenesorbitan monooleate (Tween®-80) present in an amount of about 3.2 ml/L, and the POP-POE block copolymer is Pluronic® L121 present in an amount of about 20 ml/L. Pluronic® L121 is a liquid copolymer at 1540° C., where the polyoxypropylene (POP) component has a molecular weight of 3250 to 4000 and the polyoxyethylene (POE) component comprises about 10–20%, preferably 10%, of the total molecule.

Individual raccoon poxviruses expressing the gag or env genes may be mixed together for vaccination. Furthermore, the virus may be mixed with additional inactivated or attenuated viruses, bacteria, or fungi, or with immunogens derived from viruses, bacteria, or fungi such as feline leukemia virus, feline panleukopenia virus, feline rhinotracheitis virus, feline calicivirus, feline infectious peritonitis virus, feline *Chlamydia psittaci, Microsporum canis,* or others. In addition, antigens from the above-cited organisms may be incorporated into combination vaccines. These antigens may be purified from natural sources or from recombinant expression systems, or may comprise individual subunits of the antigen or synthetic peptides derived therefrom.

In a further embodiment of the present invention, live or inactivated RRPV virus-cell lysates can be incorporated into liposomes, or encapsulated in peptide-, protein-, or polysaccharide-based microcapsules prior to administration, using means that are known in the art. The vaccine of the present invention is administered to cats in volumes ranging from 0.5 to 5 milliliters. The vaccine can be administered to cats by subcutaneous, intramuscular, oral, intradermal, or intranasal routes. The number of injections and their temporal spacing may be varied. One to three vaccinations administered at intervals of one to three weeks are usually effective.

The efficacy of the vaccines of the present invention is assessed by the following methods. At about one month after the final vaccination, vaccinates and controls are each challenged with 3–20 cat $ID_{50}$ units, preferably 5 cat $ID_{50}$ units of FIV, preferably the NCSU1 isolate (ATCC VR-2333). Whole blood is obtained from the animals immediately before challenge, and at intervals after challenge, for measurement of a) viremia and b) relative amounts of CD4 and CD8 lymphocytes.

Viremia is measured by isolating mononuclear cells from the blood, and co-culturing the cells with mononuclear cells from uninfected animals. After 7 days of culture, the culture supernatants are tested for FIV by enzyme-linked immunoassay (See Example 5 below).

The ratio of CD4 to CD8 lymphocytes in the circulation of vaccinates and controls is taken as a measure of immune function. Typically, FIV infection causes an inversion of the normal CD4:CD8 ratio of about 1.5–4.0 to a pathological ratio of about 0.5–1.0. The numbers of CD4 and CD8 lymphocytes are measured by flow cytometry using specific antibodies (see Example 5 below).

Another measure of immune function is to challenge vaccinates and controls with *Toxoplasma gondii* at 6–12 months after the final RRPV-FIV vaccination. Normally, the severity of *T. gondii*—induced disease symptoms is considerably exacerbated in FIV-infected cats relative to uninfected cats. The severity of the *T. gondii* effect is determined by scoring ocular discharge, nasal discharge, dyspnea, and fever.

It will be understood that amelioration of any of the symptoms of FIV infection is a desirable clinical goal. This includes a lessening of the dosage of medication used to treat FIV-induced symptoms.

The following examples are intended to illustrate the present invention without limitation thereof.

EXAMPLE 1

Cloning of FIV gag and env Genes

A. Isolation of Viral DNA

FIV strain NCSU-1 (designated "FIV-NCSU-1") was isolated from a naturally infected, feline leukemia virus-negative cat and has been described previously (Tompkins et al., *J. Am. Vet. Med. Assoc.* 199: 1311, 1991. The virus was passed in a normal specific pathogen-free (SPF) cat (obtained from Liberty Laboratories, Waverly,. N.Y.). FIV-infected peripheral blood mononuclear cells (PBMC) were obtained from whole blood by separation on discontinuous percoll gradients. Briefly, anti-coagulated whole blood was layered over a two step gradient containing 43% Percoll™ (Pharmacia, Piscataway, N.J.) over 62.5% Percoll™ in 0.15 M NaCl. Gradients were centrifuged at 400×g for 5 minutes, followed by 800×g for 20 minutes at 22° C. PBMC were harvested from the gradient interface and washed in phosphate buffered saline containing 5% fetal bovine serum. In parallel, PBMCs were isolated from normal cats.

FIV was propagated by co-culture of PBMCs from an FIV-infected cat with PBMCs from normal cats. The cells were maintained in RPMI 1640 media containing 10% fetal bovine serum, $2.5\times10^{-5}$ beta-mercaptoethanol, 2 mM L-glutamine, 5 μg/mL concanavalin A, and 20% conditioned media from MLA cells (ATCC TIB 201) as a source of interleukin-2 (IL2).

Cat genomic DNA containing FIV-NCSU-1 proviral sequences was isolated from the cultured PBMCs by lysis of the cells with 0.6% sodium dodecyl sulfate (SDS) in 10 mM Tris-HCl, pH 7.5, 10 mM EDTA, followed by precipitation of chromosomal DNA by incubation overnight with 1 mM NaCl. The DNA was recovered by centrifugation at 10,000 r.p.m. (Beckman J2, JA-20 rotor) for 40 minutes. The DNA pellet was resuspended in a solution containing 10 mM Tris-HCl pH 7.5, 10 mM EDTA, 0.1% SDS buffer and digested with ribonuclease A (20 μg/ml) and proteinase K (0.2 mg/ml) at 50° C. for 4 hours. DNA was then purified by sequential extraction with phenol, phenol:chloroform (1:1) and chloroform, and was recovered in pure form followed by ethanol precipitation.

B. Cloning of FIV Envelope Gene

FIV-NCSU-1 envelope DNA sequences were cloned using polymerase chain reaction (PCR) methods as follows:

Envelope Fragment A

The following oligonucleotides were used to amplify the 5' proximal segment of the env gene.
5'-TCGGATCCAACAATAATTATGGCAGAAGG-3' [SEQ. I.D. NO. 1] (Coding strand, 6252-V)
5'-AATCAGGTACAAAGTCACCGTTC-3' [SEQ. I.D. NO. 2] (Complementary strand, 6745-C)

Primer 6252-V corresponds to nucleotides 6252–6273 of FIV strain PPR (GenBank No. M36968) and primer 6745-C (underlined region) corresponds to nucleotides 6723–6745 of FIV strain 14 (GenBank No. 25381). The start codon for envelope protein translation is included in primer 6252-V. Primer 6252-V also has a synthetic BamHI restriction enzyme site near the 5' end to facilitate cloning. An AvrII site located at position 6719 also facilitates cloning. Envelope fragment A is 494 bp in length.

Envelope Fragment B

The following oligonucleotides were used to amplify the middle segment of the env gene.
5'-TATAGAAGCACCCCAAGAAGAG-3' [SEQ. I.D. NO. 3] (Coding strand, 6637-V)
5'-CATTCCCCCAAAGTTATATTTC-3' [SEQ. I.D. NO. 4] (Complementary strand, 8469-C)

Primers 6637-V and 8469-C correspond to nucleotides 6637–6659 and 8448–8469 of FIV 14 strain, respectively. An AvrII site at position 6719 and a SpeI site at position 8288 facilitated cloning. Envelope fragment B is 1833 bp in length.

Envelope Fragment C

The following oligonucleotides were used to amplify the 3' distal fragment of the env gene.
5'-TTAGTTACATTAGAGCATCAAG-3' [SEQ. I.D. NO. 5] (Coding strand, 8264-V)
5'-TTCTAGATCTTCAGGGTCCCAATACTC-3' [SEQ. I.D. NO. 6] (Complementary strand, 9145-C)

Primer 8264-V corresponds to nucleotides 8264–8285 of FIV strain 14, and primer 9145-C (underlined region) corresponds to nucleotides 9126–9145 of FIV strain PPR. Primer 9145-C has a synthetic BglII site near the 5' end to facilitate cloning. An SpeI site located at position 8288 also facilitated cloning. Envelope fragment C is 880 bp in length.

In each case, PCR was performed for 35 cycles of 1 min 30 sec at 94° C., 2 min at 56° C., and 2 min at 72° C., followed by one cycle of 8 min at 72° C. Each envelope fragment was isolated by gel electrophoresis and cloned into plasmid pSL1190 using standard methods (Maniatis et al., *Molecular Cloning: A Laboratory Manual*, 1982, Cold Spring Harbor Press).

Figure 1B:
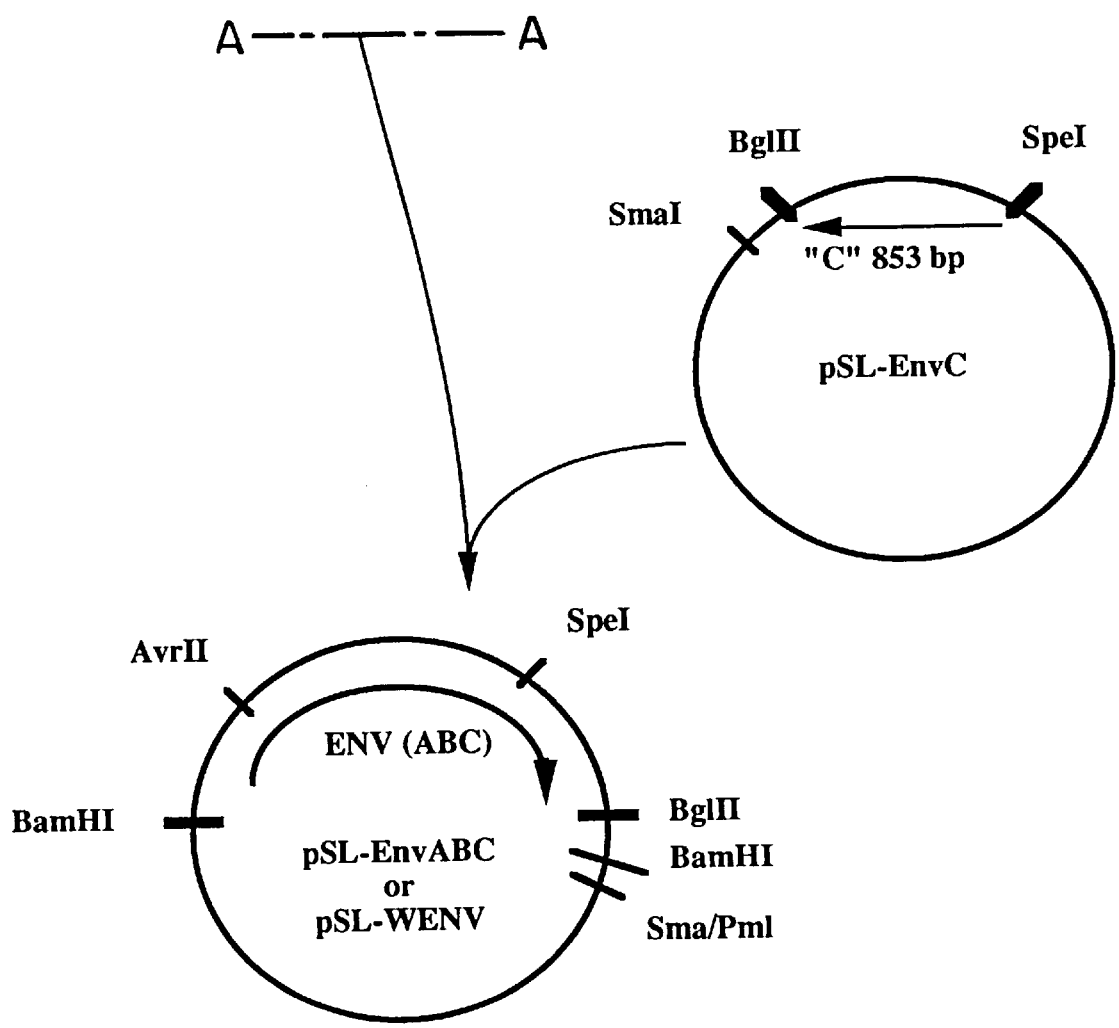

Initially, each fragment was cloned into pSL1190, after which the three fragments were spliced together to re-create a full length envelope gene. For this purpose, the Envelope A plasmid was digested with BamHI and AvrII, the envelope B plasmid was digested was with AvrII and SpeI, and the envelope C plasmid was digested with SpeI and BglII. Subsequently, the 1.5 kbp AvrII/SpeI envelope B fragment was ligated into pSL-EnvA that had been digested with AvrII and SpeI to create pSL-EnvAB (FIG. 1). The envAB fragment codes for the entire surface membrane protein (SU) and the first 63 amino acids from the amino-terminus of the transmembrane protein (TM) of FIV-NCSU-1, i.e., amino acids 1–735 of env. However, envAB does not contain the transmembrane domain (TM).

Figure 2:
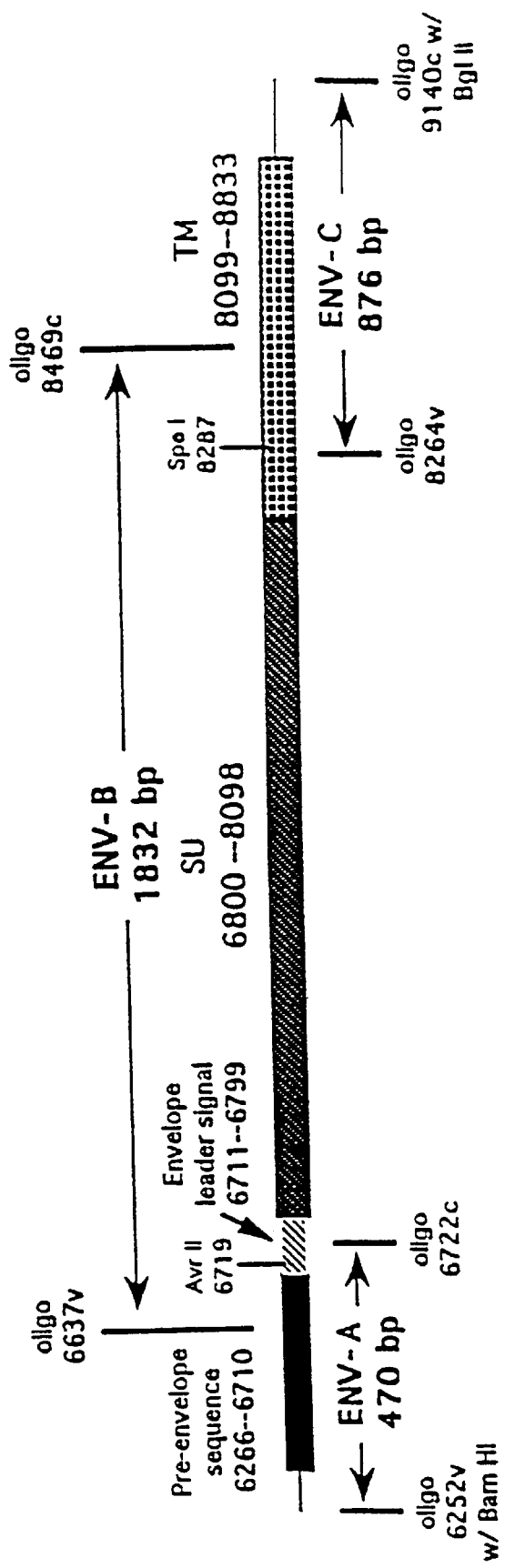
FIG. 2 is a diagrammatic representation of the structure of the recombinant FIV env gene in pSL-EnvABC.

Next, the 0.9 kbp SpeI/SmaI envelope C fragment from pSL-EnvC was ligated into pSL-EnvAB that had been digested with SpeI and BbrPI, to create pSL-EnvABC or pSL-WEnv (FIG. 1). The WEnv fragment codes for the entire env open reading frame (SU and TM proteins) of FIV NCSU-1 (FIG. 2).

Figure 3D:
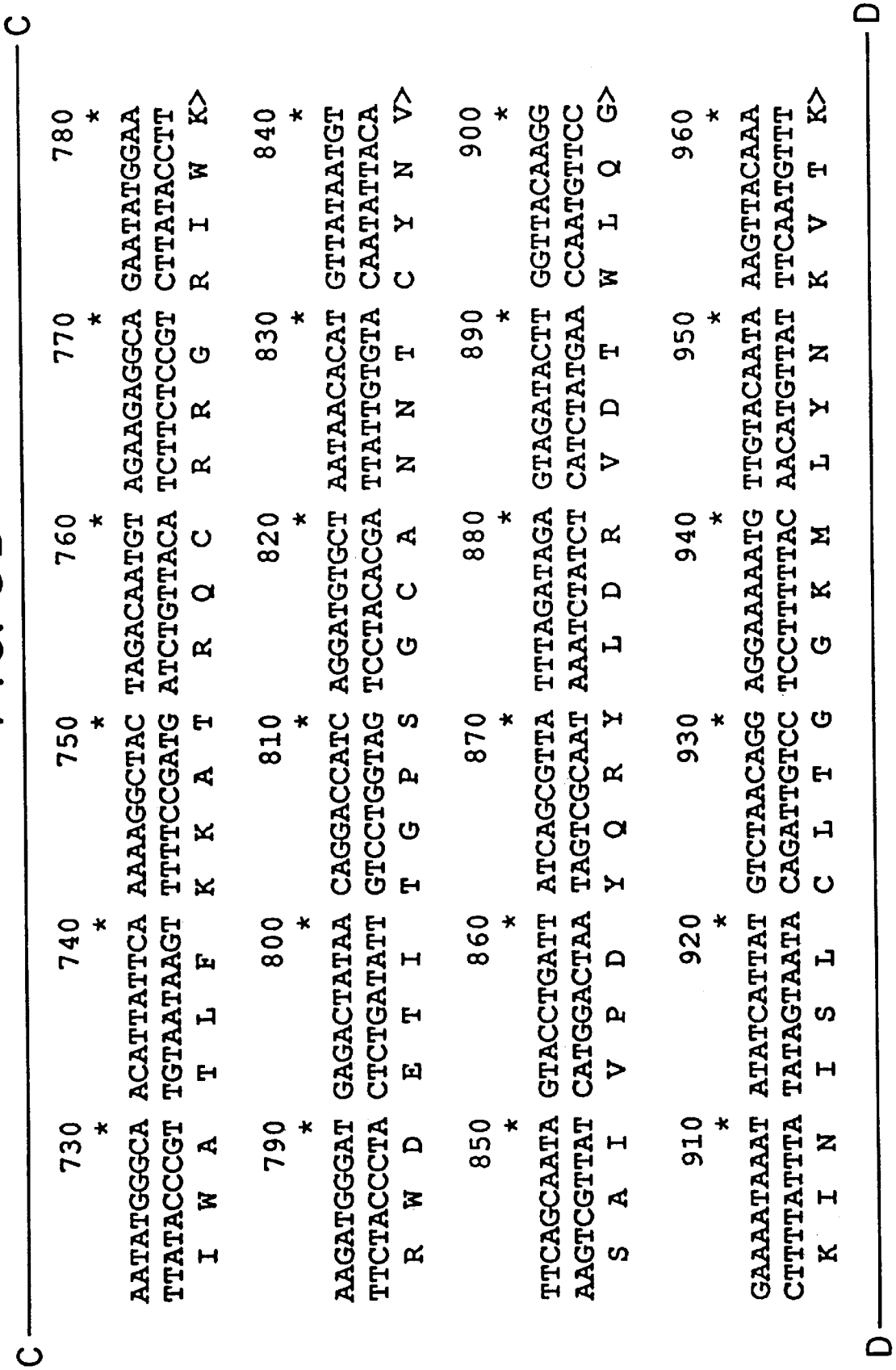

The subcloned genetic elements of FIV-NCSU-1 were sequenced using Sequenase Version 2.0 (United States Biochemical, Cleveland, Ohio)) as described for double-stranded DNA, and the reactions were analyzed using the ABI automated sequencer (Applied Biosystems, Foster City, Calif.). Both DNA strands were sequenced to confirm the results. The DNA sequences were analyzed using the MacVector DNA Analysis software (International Biotechnologies, Inc., New Haven, Conn.). The env DNA sequences were analyzed for open reading frames and compared to the previously published DNA sequences of other FIV isolates. The DNA and predicted amino acid sequences of env and envAB open reading frames of FIV-NCSU-1 are shown in FIG. 3.

C. Cloning of The FIV GAG Gene

The gag gene of FIV-NCSU$_1$ was amplified using PCR and the following oligonucleotide primers:
5'-CAATTCTAGAGAGACTCTACAGCAACATG-3' [SEQ. I.D. NO. 7] (Coding strand, 610-V)
5'-TAATAGATCTGGCCTCTTTTCTAATGATG-3' [SEQ. I.D. NO. 8] (Complementary strand, 2026-C)

Figure 4:
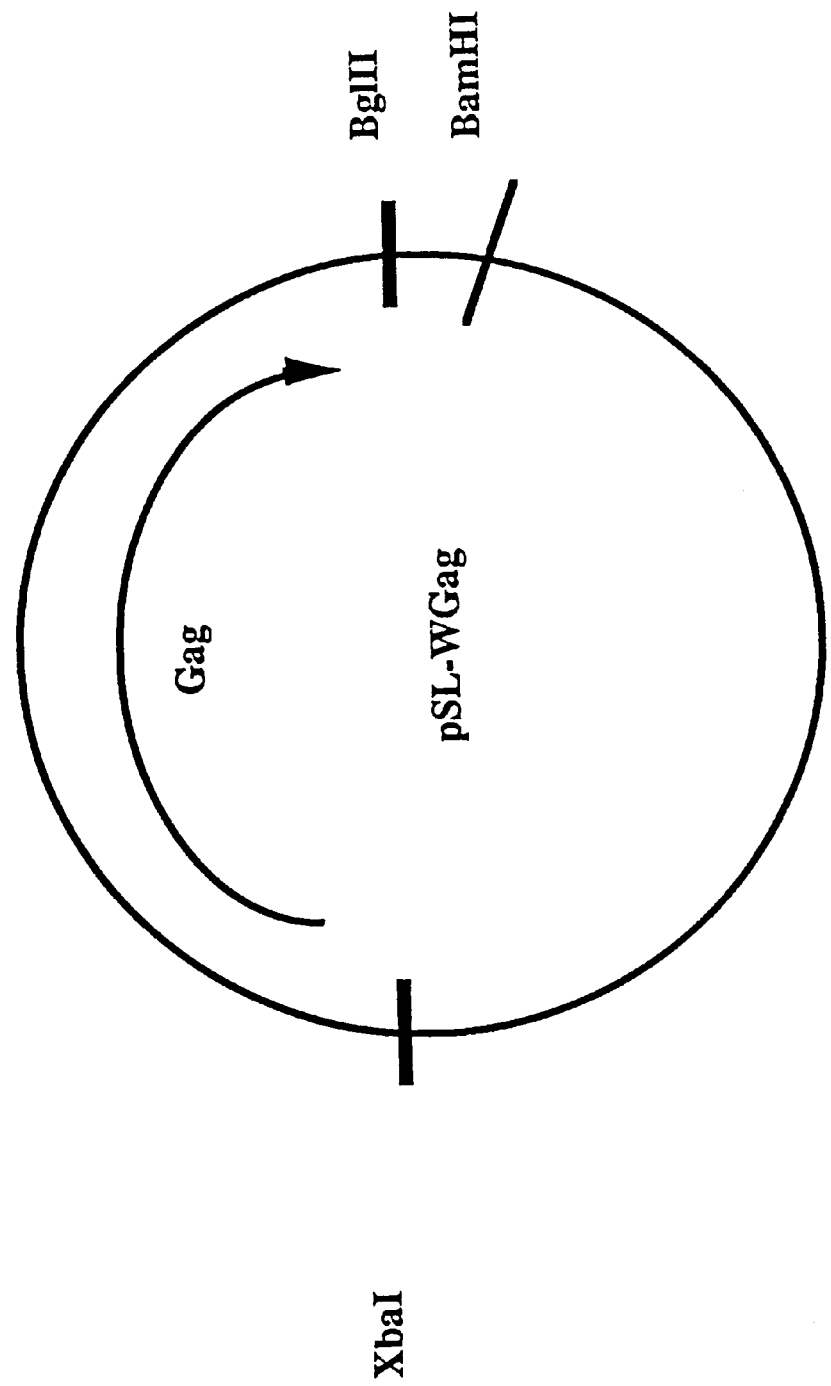
FIG. 4 is a graphic illustration of the pSLWGag plasmid.
Figure 6:
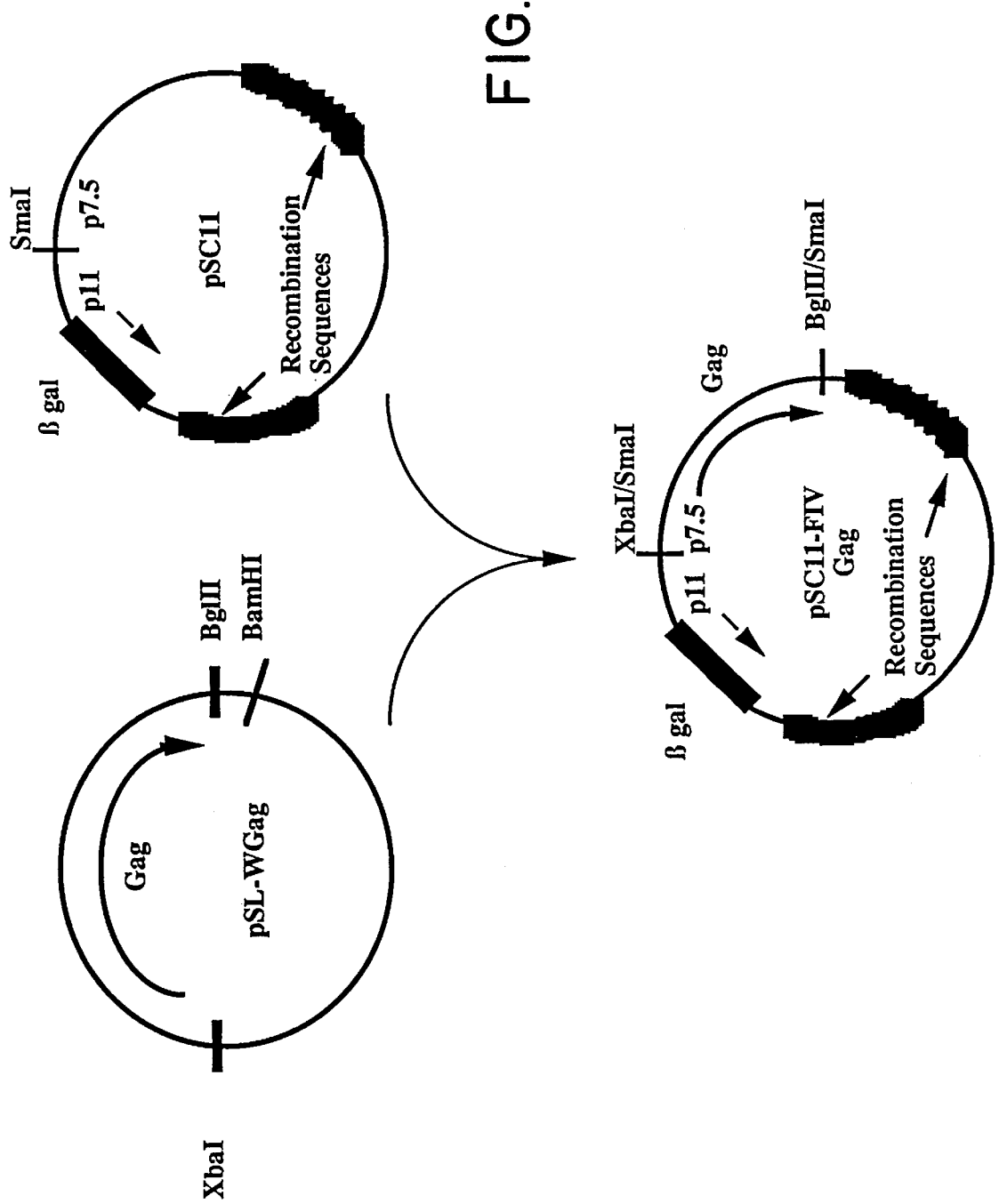
FIG. 6 is a graphic illustration of the cloning strategy for construction of the raccoon poxvirus transfer plasmid pSC11-FIV gag.

Primers 610-V and 2026-C correspond to nucleotides 610–630 and 2005-2026 of FIV 14 strain, respectively. Primers 610-V and 2026-C have XbaI and BglII restriction enzyme sites, respectively, near their 5' ends to facilitate cloning. The last three nucleotides of primer 610-V correspond to the start codon for gag protein translation. PCR was performed for 35 cycles of 1 min 30 sec at 94° C., 2 min at 56° C., and 2 min at 72° C., followed by one cycle of 4 min at 72° C. The 1.4 kbp DNA fragment containing the gag gene was purfied by gel electrophoresis and cloned into the XbaI/BglII site of pSL1190 to form pSL-WGag (FIG. 4). The DNA sequence of FIV-NCSU-1 gag is shown in FIG. 5.

EXAMPLE 2

Preparation of Recombinant Raccoon Poxviruses

A. Construction of Raccoon Poxvirus Transfer Plasmids

The DNA sequences encoding the gag, env, and envAB isolated as described in Example 1 were individually subcloned into the poxvirus transfer vector pSC11. The sequence of pSC11 is disclosed in co-pending U.S. patent application Ser. No. 08/125,516, which is incorporated by reference. For this purpose, the 1.4 kb XbaI/BglII fragment of pSL-WGag (FIG. 6), the 2.9 kb BamHl/SpiI fragment of pSL-WEnv (FIG. 7) and the 2.1 kb BamHI/SpeI fragment of pSLEnvAB (FIG. 8) were individually isolated and rendered blunt-ended with the Klenow fragment of DNA polymerase, after which each was individually cloned into the SmaI site of pSC11.

B. Preparation of Recombinant Raccoon Poxviruses

Recombinant raccoon pox viruses (RRPV) bearing the FIV gag and env genes were prepared as generally described for recombinant vaccinia viruses (Mackett and Smith, *J Gen Virol* 67:2067–2082, 1986) with some modifications. Monolayers of Vero cells (ATCC CCL 81) that were 80% confluent (approximately $5\times10^6$ cells in 100 mm tissue culture dishes) were infected with wild-type raccoon pox virus (ATCC VR-838) at a multiplicity of infection (MOI) of 0.1 $TCID_{50}$/cell in 2 ml of MEM (Eagle's Mininum Essential Medium (Gibco BRL #410-1500) containing 0.05% lactalbumin hydrolysate and 15 $\mu$g/ml gentamicin sulfate, adjusted to pH 7.2 with sodium bicarbonate) for 30–60 minutes at 37° C. The cells were then transfected with either pSC11-FIV gag, pSC11-FIV env, or pSC11-FIV env AB transfer plasmids by cationic liposome-mediated transfection using Transfectam® (Promega Corporation, Madison, Wis.) according to manufacturer's instructions. The cells/

DNA-liposomes mixture was incubated in 3 ml of MEM containing 0.5% fetal bovine serum (FBS) overnight at 37° C. (5% $CO_2$), after which the medium was replaced with 8 ml fresh MEM/5% FBS. The transfected cells were incubated at 37° C. (5% $CO_2$) until greater than 80% of the cells showed cytopathic effects (approximately 34 days). The cells and culture media (viral-cell lysates) were then removed from the plates and subject to two cycles of freeze-thawing before storage at −70° C.

C. Isolation of Recombinant Raccoon Pox Virus Carrying the FIV gag Gene

RRPV carrying the FIV-$NCSU_1$gag gene (RRPV-FIV gag) are isolated and purified from the pSC11-FIV gag/Vero cell transfection by standard viral plaque assay methods. Monolayers of Vero cells (50–80% confluent) in 100 mm tissue culture dishes were infected with 2 ml of 10-fold serial dilutions ($10^{-1}$ to $10^{-3}$ in MEM) of the viral-cell lysates. After incubation, for 1 hour at 37° C., the media are removed and the infected cells were overlaid with 8–10 ml of 1.25% Noble agar containing MEM/5% FBS. The infected cells were then incubated for 34 days at 37° C. (5% $CO_2$), and overlaid again with 4 ml of 1.25% Nobel agar containing 0.5X PBS and 600 ug/ml 5-bromo4-chloro-3-indolyl-β-D-galactopyranoside (X-gal, United States Biochemical, Cleveland, Ohio). The plates were incubated at 37° C. (5% $CO_2$) for 4–16 hours, until blue viral plaques (β-galactosidase positive) were observed. The recombinant viral plaques were picked with sterile blunt needles attached to a 1 cc syringe, suspended in 0.5 ml of 0.25 mg/ml trypsin, vortexed vigorously, and incubated at 37° C. for 15–30 minutes. The disrupted viral plaques were then inoculated onto $5 \times 10^5$ Vero cells in T-25 $cm^2$ flasks and incubated at 37° C. (5% $CO_2$) until greater than 80% CPE was observed. The viral-cell lysates containing RRPV-FIV gag were subjected to two cycles of freeze-thawing and stored at −70° C. Five individual RRPV-FIV gagclones were selected and plaqued purified four times as described above.

D. Isolation of Recombinant Raccoon Pox Virus Carrying FIV envAB Gene

RRPV carrying the FIV-$NCSU_1$ envAB gene (RRPV-FIV envAB) were isolated and purified from the pSC11-FIV envAB/Vero cell transfection using the methods as described for RRPV-FIV gag with some slight modifications. Thymidine kinase deficient (tk-) raccoon pox viruses from the initial viral-cell lysates were selected on tk- Rat-2 cells (ATCC CRL 1764). This was performed by inoculating 1 ml of the initial viral-cell lysate onto a monolayer of Rat-2 cells in a T-75 $cm^2$ flask (approximately $5 \times 10^6$ cells) containing 5-bromodeoxyuridine (BrdU) at 30 ug/ml in MEM. The infected monolayer was incubated at 37° C. (5% $CO_2$) for 3–4 days until greater than 70% CPE was observed. The tk- viral-cell lysates were subjected to two cycles of freeze-thawing two times and stored at −70° C. RRPV-FIV envAB were isolated and purified from the tk- viral-cell lysates by the standard viral plaque assay as described above for RRPV-FIV gag on Vero cells. Five individual RRPV-FIV env AB clones were selected and plaque purified five times.

EXAMPLE 3

Characteristics of Recombinant FIV-Expressing Raccoon Pox Viruses

A. Confirmation of FIV gag and envAB Genes in RRPV by Polymerase Chain Reaction

The presence of the FIV gag and envAB genes in the RRPVs was confirmed sing PCR. 90 μl of a viral-cell lysate was incubated with 10 μl of 10× PCR lysis buffer 1×; 10 mM Tris-HCl buffer, pH 8.5, containing 50 mM KCl, 2.5 mM $MgCl_2$, 0.5% Tween 20, 0.3 mg/ml Proteinase K) for 16 hours at 50° C., then boiled for 10 minutes. 10 μl of this lysate was used as a template in the PCR reaction. PCR was performed in 100 μl of 10 mM Tris-HCl buffer, pH 8.3, containing 50 mM KCl, 200 uM of each dNTP, 1.5 mM $MgCl_2$, 30 pmoles of each primer, and 2.5 Units of Ampli-Taq® DNA polymerase (Perkin-Elmer Cetus, Norwalk, Conn.). The primers used in the PCR for FIV gag were:

5'-TATGGAAAAGGCAAGAGAAGGAC-3' [SEQ. I.D. NO. 9]

5'-TCGAGATACCATGCTCTACACTG-3' [SEQ. I.D. NO. 10]

corresponding to nucleotides 471–493 and 763–785 of the FIV gag open reading frame, respectively. The primers used in the PCR for FIV envAB were:

5'-TATGGAAAAGATGGGATGAGACTA-3' [SEQ. I.D. NO. 11]

5'-GTCACTTACCTTCATAGTAAACC-3' [SEQ. I.D. NO. 12]

corresponding to nucleotides 857–880 and 1513–1535 of the FIV env open reading frame, respectively. The PCR amplifications were performed in a DNA Thermal Cycler (Perkin-Elmer Cetus) by first heating the reaction mixes to 94° C. for denaturation, and then 35 cycles of 1 minute at 95° C., 1 minute at 55° C., and 2 minutes at 72° C., and a final incubation of 8 minutes at 72° C. 10 μl of the PCR products were analyzed by electrophoresis in a horizontal-submarine 4% NuSieve® agarose (FMC BioProducts, Rockland, Me.) gel in TAE buffer (40 mM Tris base, 20 mM sodium acetate, 1 mM EDTA, pH 7.2) by applying 5 V/cm for 1–2 hours, and staining with ethidium bromide. PCR amplifications with the FIV gag and env primers gave expected DNA fragments of 314 and 678 nucleotides, respectively. PCR amplifications using the pSC11 FIV gag and envAB transfer plasmids served as positive controls. PCR amplifications using wild-type raccoon pox virus-Vero cell lysates served as a negative control.

B. Confirmation of RRPV FIV gag and envAB Protein Expression by Western Blot Analysis Confluent monolayers of Vero cells in a T-25 $cm^2$ flask ($1–2 \times 10^6$ cells) were infected with clones of either RRPV-FIV gag or RRPV-FIV envAB at an M.O.I. of 1 to 10 $TCID_{50}$ per cell. The infected cells were incubated at 37° C. (5% $CO_2$) for 2–3 days until approximately 80% CPE was observed. 20 μl of the viral-cell lysate was added to 5 μl of 5× Laemmli sample buffer (0.3 M Tris-HCl buffer, pH 6.8, containing 5% SDS, 50% glycerol, 0.4% bromophenol blue, and 3% 2-mercaptoethanol) and heated at 95° C. for 5 minutes. The denatured protein samples were separated by SDS/polyacrylamide electrophoresis using a 4–15% gradient polyacrylamide gel (Maniatis et al., Molecular Cloning: A Laboratory Manual, 1982, Cold Spring Harbor Press). After electrophoresis, the proteins were transferred to nitrocellulose filters (Bio-Rad Laboratories, Hercules, Calif.) by electrotransfer using a Bio-Rad transfer apparatus per manufacturer's instructions. The transfer was performed in 25 mM Tris-HCl buffer, containing 0.2 M glycine and 20% methanol, for 45 minutes at 50V with constant current.

The blot was then screened for FIV gag and envAB proteins by immunoblot analysis as previously described (Davis et al., Basic Methods in Molecular Biology, 1986, Elsevier Science Publishing Company, New York, N.Y.) with some slight modifications. After transfer, the nitrocellulose blot was rinsed in phosphate buffer saline, pH 7.4, containing 0.1% Tween-20 (PBS-TW), and non-specific sites were blocked by incubating the blot in PBS containing 1% bovine serum albumin (PBS-BSA) at 4° C. overnight, followed by a 15 minute wash in PBS-TW. The blot was then incubated for 30 minutes at room temperature with goat anti-FIV IgG diluted 1:100 in PBS-TW containing 1% BSA (PBS-TW-BSA), followed by four 5 minute washes in PBS-TW. Next, the blot was incubated for 30 minutes at room temperature with a biotin-labeled mouse-anti-goat IgG antibody (secondary antibody) (Kirkegaard & Perry Laboratories Inc., Gaithersburg, Md.) diluted 1:2000 in PBS-TW-BSA, followed by four 5-minute washes in PBS-TW. Antigen-antibody complexes were detected by, incubating the blot for 30 minutes at room temperature with horseradish peroxidase conjugated streptavidin (Kirkegaard & Perry Laboratories Inc.) diluted 1:1000 in PBS-TW, washing four times for 5 minutes each in PBS-TW, and visualizing with peroxidase chromogenic substrate (Kirkegaard & Perry Laboratories Inc.). Sucrose-gradient purified FIV and wild-type raccoon pox virus/Vero cell lysates were used as the positive and negative controls for the immunoblot analysis, respectively.

Goat anti-FIV antibodies were prepared as follows. FIV $NCSU_1$ was grown in peripheral blood lymphocytes and concentrated using a hollow fiber apparatus to a concentration of about $10^6$ $TCID_{50}$/ml. The concentrated virus stock was mixed with an oil adjuvant such as OW3 in a ratio of 1:1 (v:v), and the emulsion was used to inoculate goats six times, at intervals of 34 weeks. At monthly intervals, the goats were bled and the serum was tested for the presence of anti-FIV antibodies.

C. Confirmation of RRPV FIV gag and envAB Protein Expression by Immunofluorescence Assay Confluent monolayers of Vero cells in 96-well plates ($1-2 \times 10^4$ cells/well) are infected with clones of either RRPV-FIV gag or RRPV-FIV envAB at a multiplicity of infection of 0.1 to 1.0 plaque forming units per cell. Cell infected with wild-type RCNV serve as a negative control. The infected cells are incubated at 37° C. (5% $CO_2$) for 1 day until approximately 20% CPE is observed. The cells are then washed three times with PBS and fixed with 80% acetone at 4° C. for ten minutes. Next, the cells are rehydrated with PBS and incubated with a monoclonal antibody (IgG) against either FIV gag or env surface membrane proteins for 30 minutes at room temperature. FIV antigen/FIV antibody complexes are detected using a FITC-conjugated goat anti-mouse IgG (Kirkegaard & Perry Laboratories Inc., Gaithersburg, Md.) and fluorescence microscopy.

D. Raccoon Poxvirus Titration

Virus preparations were pre-treated by dilution into an equal volume of 0.5% trypsin and incubation at 37° C. for 30 minutes in order to release virus from inclusions. Serial dilutions (10-fold) of virus were then prepared in MEM and were inoculated (100 μl/well) in replicates of five onto Vero cells (1×$10^4$ cells in 100 μl per well) in a 96 well plate. Plates were incubated for 3–5 days at 37° C. (5% $CO_2$) and observed for cytopathology typical of raccoon poxvirus. Viral infectivity titers were calculated as 50% endpoints based on cytopathology using the methods of Reed and Muench (Reed and Muench, *The American Journal of Hygiene* 27: 493, 1938).

EXAMPLE 4

Preparation of Vaccines Based on Recombinant Pox Viruses

A. Preparation of Master Seeds of RRPV-FIV gag and envAB Viruses

A single clone of each recombinant virus that showed significant recombinant protein expression (by the method described in Example 3 above) was selected for large-scale expansion to serve as a master seed virus. All recombinant virus expansions and titrations were done on Vero cells in MEM containing 2.5% FBS. Each plaque-purified virus clone was expanded by inoculating a confluent monolayer of Vero cells in a T-150 $cm^2$ flask (1×$10^7$ cells) with 1 ml of viral-cell lysate (approximately $10^7$ infectious virus particles), and incubating at 37° C. (5% $CO_2$) until 100% CPE was observed (2–3 days). This viral-cell lysate served as a pre-master seed virus stock and was used to obtain the master seed virus. The pre-master seed of each recombinant virus was titrated on Vero cells and a $TCID_{50}$ was determined. The master seed viruses for RRPV-FIV gag and RRPV-FIV envAB were grown on Vero cells using an MOI of 0.01 and 0.1, respectively. Three roller bottles of confluent Vero cells were infected for each of the master seed viruses using MEM media supplemented with 2.5% fetal bovine serum and incubated for approximately 3 days at 37° C. Infected culture supernatant fluids were harvested, and seed viruses were aliquoted into 1.5 ml ampules, which were sealed and stored in a liquid nitrogen freezer.

B. Preparation of Vaccines

Vero cells (3×$10^7$) were seeded into 850 $cm^2$ roller bottles in 200 ml of growth media (MEM containing 0.5% lactalbumin hydrolysate and 5% heat-inactivated fetal bovine serum) and incubated for 18 hours at 37° C. The next day, the media were removed from the cells and replaced with 50 ml of RRPV-FIV gag at a multiplicity of infection of 0.01 in infection media (MEM containing 0.5% LAH and 2.5% heat-inactivated fetal bovine serum). The virus used was at the fourth passage beyond the master seed preparation. Virus was allowed to adsorb to the cells for 30 minutes at 37° C., after which the volume of medium was adjusted to 150 ml per roller bottle. Roller bottles were incubated at 37° C. until 100% cytopathology was evident (3 days). A virus/cell lysate was then prepared and stored frozen (−70° C.). The virus titer of RRPV-FIV gag was determined to be 1074 $TCID_{50}$/ml.

Recombinant raccoon poxviruses expressing the FIV envAB gene fragment were prepared in the same manner, except that a multiplicity of infection of 0.1 was used. The virus was at the fourth passage beyond the master seed preparation. The RRPV-FIV envAB preparation was titered and found to contain $10^{6.4}$ $TCID_{50}$/ml.

Wild type raccoon poxvirus was grown using the same methods as described above. This virus preparation was found to contain $10^{7.7}$ $TCID_{50}$/ml.

EXAMPLE 5

Test of Efficacy of FIV Vaccines Based on Recombinant Pox Viruses

A. Vaccination

Thirty 6–7 month old cats (specific pathogen-free, Harlan Sprague Dawley, Madison, Wis.), fifteen males and fifteen females, were used. Cats were divided into six groups and vaccinated twice, 21 days apart, as indicated below:

TABLE 1

Assignment of Groups for Vaccination

| Group | # Cats | Vaccine | Volume | Virus Dose ($TCID_{50}$) | Route* |
|---|---|---|---|---|---|
| 1 | 5 | RRPV-FIV gag | 1 mL | $10^{7.4}$ | SC |
| 2 | 5 | RRPV-FIV gag | 1 mL | $10^{7.4}$ | IM |
| 3 | 5 | RRPV-FIV envAB | 3 mL | $10^{6.9}$ | SC |

TABLE 1-continued Assignment of Groups for Vaccination

| Group | # Cats | Vaccine | Volume | Virus Dose (TCID$_{50}$) | Route* |
|---|---|---|---|---|---|
| 4 | 5 | RRPV-FIV envAB | 2 mL | 10$^{6.7}$ | IM |
| 5 | 5 | RRPV-FIV gag(1 ml) + | 4 mL | 10$^{7.4}$ (gag) | SC |
|   |   | RRPV-FIV envAB | 3 mL | 10$^{6.9}$ (envAB) | SC |
| 6 | 5 | Wild Type raccoon pox virus | 1 mL | 10$^{7.7}$ | SC |

*SC = Subcutaneous Vaccination
IM = Intermuscular Vaccination

B. Experimental Design

Twenty-five cats were vaccinated with the recombinant raccoon poxvirus vaccines as indicated in Table 1. Five cats were administered a similar titer of wild type raccoon poxvirus to serve a negative controls. Two vaccinations were administered 21 days apart. Subcutaneous vaccinations were administered in the nape of the neck, and intramuscular vaccinations were administered in a rear thigh. Four weeks following the second vaccination, all cats were challenged with the NCSU-1 strain of FIV and monitored for viremia and evidence of lymphocyte population changes as described below. Eleven months following FIV challenge, cats in Groups 1, 2, 3, 4, and 6 were challenged with Toxoplasma gondii and monitored for 48 days for clinical signs of disease.

C. FIV Challenge

Four weeks following the second vaccination, all of the cats were challenged subcutaneously with 10 cat ID$_{50}$ units of the NCSU$_1$ isolate of FIV(1: 1000 dilution of lot # 021891). Whole blood was obtained from the cats prior to challenge, and periodically after challenge, in order to assess virus infection parameters as follows:

1. Detection of Viremia

Culture isolation of FIV was performed as described previously (Wasmoen et al., *Vet. Immuno. Immunopath.* 35:83 1992). Mononuclear cells were isolated from whole blood using Percoll™ (Pharmacia Biotech, Piscataway N.J.) gradients. 5×10$^5$ cells from FIV-challenged cats were cultured with 1×10$^6$ mononuclear cells isolated from uninfected cats. Cultures were fed with RPMI media every 7 days and supernatants tested for the presence of FIV by an enzyme-linked immunosorbent assay (ELISA) that detects FIV p25 antigen (Petcheck ELISA, IDEXX, Portland Me.).

2. Lymphocyte Subsets

Leukocytes were isolated from whole blood using Histopaque™ (Sigma Chemical Company, St. Louis Mo.) and lymphocyte subsets quantitated by staining the cells with antibodies specific to CD4 (monoclonal antibody CAT30A), CD8 (monoclonal antibody FLSM 3.357), pan T lymphocytes (monoclonal antibody FLSM 1.572) or B lymphocytes (anti-cat IgG) followed by FACS analysis. These monoclonal antibodies are described elsewhere (Tompkins et al. *Vet. Immunol. Immunopathol.* 26:305, 1990) and the flow cytometry procedure is the same as previously described (R. V. English et al. *J. Infect. Dis.* 170:543, 1994). CD4:CD8 ratios were calculated.

D. *Toxoplasma gondii* Challenge

Tacheozoites of the ME49 strain of *T. gondii* that were frozen in 10% glycerol were inoculated intraperitoneally into Swiss mice (Charles Rivers Laboratories) and serially passed in mice according to published procedures (Davidson et al., *Am. J. Pathol.* 143:1486, 1993). Tacheozoites harvested from peritoneal fluids of mice were enumerated using a hemacytometer. Cats were tranquilized using ketamine hydrochloride and inoculated with 50,000 fresh tachyzoites into the right common carotid artery that had been surgically isolated. Cats were monitored for clinical signs of disease, including ocular discharge, nasal discharge, dyspnea, fever, depression, and weight loss for 3 days prior to and 48 days following *T. gondii* inoculation.

Clinical signs follow *T. gondii* challenge were scored as follows:

| Clinical Sign | Score | |
|---|---|---|
| Fever | 103.0 to 103.9° F. | 1 point per day |
|  | 104.0 to 104.9° F. | 2 points per day |
|  | ≧105.0° F. | 3 points per day |
| (Temperatures were not scored until ≧1° F. above baseline.) | | |
| Depression/Lethargy |  | 1 point per day |
| Dehydration |  | 2 points per day |
| Nasal Discharge |  | 1 point per day |
| Ocular Discharge |  | 1 point per day |
| Respiratory Distress: |  |  |
| Tachypnea |  | 2 points per day |
| Dyspnea |  | 4 points per day |

E. Results

At one month following inoculation with the NCSU-1 strain of FIV, 60% of the control cats were found to be viremic (FIG. 9). Cats vaccinated with RRPV-FIV gag were all negative for FIV, 40% of the cats vaccinated with RRPV-FIV envAB were virus positive, and 20% of the cats vaccinated with a combination of these two viruses were viremic (FIG. 9). Therefore, the ability of the test vaccines to prevent viremia at this time point varied from 33% to 100% (FIG. 10).

At three months after FIV challenge, 80% of the control cats were found to be virus positive (FIG. 9). Similarly, FIV could be isolated from peripheral blood mononuclear cells of nearly all vaccinated cats using this very sensitive method (FIG. 9).

With respect to immune status, 80% of the control cats showed evidence of CD4:CD8 lymphocyte ratio inversions (i.e. ratios less than 1.0) at three months (FIG. 9). In contrast, only 30% of the RRPV-gag vaccinated cats had evidence of significant CD4:CD8 inversions, and the RRPV-FIV envAB vaccinates were similarly protected from this lymphocyte subset change (FIG. 9). Cats vaccinated with a combination of the two recombinant viruses were not significantly different from the controls (i.e. 80% showed CD4:CD8 inversions) at 3 months after challenge (FIG. 9).

At 9 months after FIV challenge, 100% of the control cats were FIV infected, and all showed CD4:CD8 inversions (FIG. 9). A large percentage of the vaccinated cats were also shown to be viremic at this time point. However, only 50% of the RRPV-FIV gag vaccinates and 20% of the RRPV-FIV envAB vaccinates showed evidence of CD4:CD8 inversions at this time point. Therefore, these two vaccines showed a significant ability to prevent the CD4:CD8 lymphocyte ratio changes associated with FIV infection even though the cats appeared to be viremic (FIG. 10).

In order to determine whether CD4:CD8 lymphocyte subset inversions signified a deterioration in the immune system of cats following FIV infection (and, conversely, that lack of inversion in vaccinates signified maintenance of immune function), vaccinated and control cats (from groups 1, 2, 3, 4, and 6) were challenged with *Toxoplasma gondii*. This parasite causes subclinical infections in normal cats, but has been reported to cause severe disease in cats that are immunocompromised due to FIV infection (Davidson et al., *Am. J. Pathol.* 143:1486, 1993). Following *T. gondii* challenge, control cats displayed ocular discharge, nasal discharge, dyspnea, and fever. The average total clinical score for control cats was 15.6 (FIG. 11). By comparison, there was a 41% reduction in clinical disease scores in RRPV-FIV gag vaccinated cats, related to reductions in clinical signs of ocular discharge and dyspnea (FIG. 11). The clinical picture following *T. gondii* challenge was even less severe in RRPV-FIV envAB vaccinated cats. This group showed a 92% decrease in ocular signs, 75% decrease in nasal discharge, 73% reduction in dyspnea, and 58% decrease in overall clinical scores (FIG. 11). Further, 80% of the control cats displayed weight loss in the first 14 days after challenge, compared to weight loss in only 44% of the RRPV-FIV gag vaccinates and 50% of the V-FIV envAB vaccinates. Therefore, control cats were more susceptible to induction of disease by this opportunistic pathogen than vaccinated cats.

These data suggest that vaccination altered the progression of clinical disease caused by this virus (i.e. induction of immune suppression). This is indicated by a lower rate of CD4:CD8 inversions in vaccinated cats and by a decreased susceptibility to infection with the opportunistic pathogen *T. gondii*.

SEQUENCE LISTING

```
<160> NUMBER OF SEQ ID NOS: 16

<210> SEQ ID NO 1
<211> LENGTH: 29
<212> TYPE: DNA
<213> ORGANISM: Feline Immunodeficiency Virus

<400> SEQUENCE: 1
tcggatccaa caataattat ggcagaagg                                   29

<210> SEQ ID NO 2
<211> LENGTH: 23
<212> TYPE: DNA
<213> ORGANISM: Feline Immunodeficiency Virus

<400> SEQUENCE: 2
aatcaggtac aaagtcaccg ttc                                         23

<210> SEQ ID NO 3
<211> LENGTH: 22
<212> TYPE: DNA
<213> ORGANISM: Feline Immunodeficiency Virus

<400> SEQUENCE: 3
tatagaagca ccccaagaag ag                                          22

<210> SEQ ID NO 4
<211> LENGTH: 22
<212> TYPE: DNA
<213> ORGANISM: Feline Immunodeficiency Virus

<400> SEQUENCE: 4
cattccccca aagttatatt tc                                          22

<210> SEQ ID NO 5
<211> LENGTH: 22
<212> TYPE: DNA
<213> ORGANISM: Feline Immunodeficiency Virus

<400> SEQUENCE: 5
ttagttacat tagagcatca ag                                          22

<210> SEQ ID NO 6
<211> LENGTH: 27
<212> TYPE: DNA
<213> ORGANISM: Feline Immunodeficiency Virus

<400> SEQUENCE: 6
ttctagatct tcagggtccc aatactc                                     27
```

-continued

```
<210> SEQ ID NO 7
<211> LENGTH: 29
<212> TYPE: DNA
<213> ORGANISM: Feline Immunodeficiency Virus

<400> SEQUENCE: 7
caattctaga gagactctac agcaacatg                                        29

<210> SEQ ID NO 8
<211> LENGTH: 29
<212> TYPE: DNA
<213> ORGANISM: Feline Immunodeficiency Virus

<400> SEQUENCE: 8
taatagatct ggcctctttt ctaatgatg                                        29

<210> SEQ ID NO 9
<211> LENGTH: 23
<212> TYPE: DNA
<213> ORGANISM: Feline Immunodeficiency Virus

<400> SEQUENCE: 9
tatggaaaag gcaagagaag gac                                              23

<210> SEQ ID NO 10
<211> LENGTH: 23
<212> TYPE: DNA
<213> ORGANISM: Feline Immunodeficiency Virus

<400> SEQUENCE: 10
tcgagatacc atgctctaca ctg                                              23

<210> SEQ ID NO 11
<211> LENGTH: 24
<212> TYPE: DNA
<213> ORGANISM: Feline Immunodeficiency Virus

<400> SEQUENCE: 11
tatggaaaag atgggatgag acta                                             24

<210> SEQ ID NO 12
<211> LENGTH: 23
<212> TYPE: DNA
<213> ORGANISM: Feline Immunodeficiency Virus

<400> SEQUENCE: 12
gtcacttacc ttcatagtaa acc                                              23

<210> SEQ ID NO 13
<211> LENGTH: 1353
<212> TYPE: DNA
<213> ORGANISM: Feline Immunodeficiency Virus

<400> SEQUENCE: 13
atggggaatg gacaggggcg agattggaaa atggccatta agagatgtag taatgctgct      60
gtaggagtag gggggaagag taaaaaattt ggggaaggga atttcagatg gccattaga      120 atggctaatg tatctacagg acgagaacct ggtgatatac cagagacttt agatcaacta     180
aggttggtta tttgcgattt acaagaaaga gaaaaaaaat ttggatcttg caaagaaatt     240
gataaggcaa ttgttacatt aaaagtcttt gcggcagtag gactttttaaa tatgacagtg     300 tcttctgctg ctgcagctga aaatatgttc actcagatgg gattagacac tagaccatct     360
```

```
atgaaagaag caggaggaaa agaggaaggc cctccacagg catttcctat tcaaacagta      420
aatggagtac cacaatatgt agcacttgac ccaaaaatgg tgtccatttt tatggaaaag      480
gcaagagaag gattaggagg tgaggaagtt cagctatggt tcactgcctt ctctgcaaat      540
ttaacaccta ctgacatggc cacattaata atggccgcac cagggtgcgc tgcagataaa      600
gaaatattgg atgaaagctt aaagcaactt actgcaggat atgatcgtac acatcccct      660 gatgctccca gaccattacc ctattttact gcagcagaaa ttatgggtat tggatttact      720
caagaacaac aagcagaagc aagatttgca ccagctagga tgcagtgtag agcatggtat      780
ctcgagggac taggaaaatt gggcgccata aaagctaagt ctcctcgagc tgtgcagtta      840
agacaaggag ctaaggaaga ttattcatcc tttattgaca gattgtttgc ccaaatagat      900
caagaacaaa atacagctga agttaagtta tatttaaaac agtcattaag catggctaat      960
gctaatgcag aatgtaaaaa gccaatgacc caccttaagc cagaaagtac cctagaagaa     1020
aagttgagag cttgtcaaga aataggctca ccaggatata aaatgcaact cttggcagaa     1080
gctcttacaa aagttcaagt agtgcaatca aaaggatcag accagtgtgt ttttaattgt     1140
aaaaaaccag gacatctagc aagacaatgt agagaagtga gaaatgtaa taaatgtgga     1200 aaacctggtc atgtagctgc caaatgttgg caaggaaata gaaagaattc gggaaactgg     1260 aaggcgggc gagctgcagc cccagtgaat caagtgcagc aagcagtaat gccatctgca     1320
cctccaatgg aggagaaact attggattta taa                                 1353

<210> SEQ ID NO 14
<211> LENGTH: 3225
<212> TYPE: DNA
<213> ORGANISM: Feline Immunodeficiency Virus

<400> SEQUENCE: 14
ggatccaaca ataattatgg cagaaggatt tgcagccaat agacaatgga taggaccaga      60
agaagctgaa gagttattag attttgtat agcaacacaa atgaatgaag aagggccact      120
aaatccaggg atgaacccat ttagggtacc tggaataaca gataaagaaa agcaagacta      180
ttgtaacata ttcaaccta gttacaagat tttacggaat gaacttcaag aggtaaaact      240
agaagaagga atgcaggta agtttagaag aacaagattt ttaaggtatt ctgatgaaca      300
agtattgtcc ccggttcatg cgttcatagg atattgtatt tatttaggta atcgaaataa      360
gttaggatct ttaagacatg acattgatat tgaagcaccc cccgaagagt gttatgataa      420
tagagagaag ggtacaactg acaatataaa atatggtaga cgatgttgcc taggaacggt      480
gactttgtac ctgattttat ttataggatt aataatatat tcacagacag ccgacgctca      540
ggtagtatgg agacttccac cattagtagt cccagtagaa gaatcagaaa taattttttg      600
ggattgttgg gcaccagaag aacccgcctg tcaggacttt cttggggcaa tgatacatct      660
aaaagctaag acaaatataa gtatacgaga gggacctacc ttggggaatt gggctagaga      720
aatatgggca acattattca aaaaggctac tagacaatgt agaagaggca gaatatggaa      780
aagatgggat gagactataa caggaccatc aggatgtgct aataacacat gttataatgt      840
ttcagcaata gtacctgatt atcagcgtta tttagataga gtagatactt ggttacaagg      900
gaaaataaat atatcattat gtctaacagg aggaaaaatg ttgtacaata agttacaaaa     960
acaattaagc tattgtacag acccattaca atcccactg atcaattata catttggacc     1020
taatcaaaca tgtatgtgga atacttcaca aattcaggac cctgaaatac acaatgtgg     1080
```

-continued

```
atggtggaat cacatggcct attataacag ttgtaaatgg gaagaggcaa aggtaaagtt    1140
tcattgtcaa agaacacaga gtcagcctgg gtcatggcgt agagcaatct cgtcatggaa    1200
acaaagaaat agatgggagt ggagaccaga ttttgagagt gaaaaggtga aaatatctct    1260
acagtgcaat agcacgaaaa acctaacctt tgcaatgaga agttcaggag attatggaga    1320
agtaacggga gcttggatag agtttggatg tcatagaaat aaatcaaacc ttcatactga    1380
agcaaggttt agaattagat gtagatggaa tgtagggagt gatacctcgc tcattgatac    1440
atgtggaaac actccaaatg tttcaggtgc gaatcctgta gattgtacca tgtattcaaa    1500
taaaatgtac aagttttctt taccaaacgg gtttacaatg aaggtagatg accttattat    1560
gcatttcaat atgccaaaag ctgtagaaat gaataatatt gctggaaatt ggtcttgtac    1620
atctgacttg ccatcgtcat gggggtatat gaattgtaat tgcccaaata gtagtagtag    1680
ttatagtggt actaaaatgg catgtcctag caatcgaggc atcttaagga attggtataa    1740
cccagtagca ggattacgac aatccttaga acagtatcaa gttgtaaaac aaccagatta    1800
cttactggtc ccagaggaag tcatggaata taaacctaga aggaaaaggg cagctattca    1860
tgttatgttg gctcttgcaa cagtattatc tattgccggt gcagggacgg gggctactgc    1920
tatagggatg gtaacacaat accaccaagt tctggcaacc catcaagaat ctatggaaaa    1980
ggtgactgaa gccttagaga taaacaactt aaggttagtt acattagagc atcaagtact    2040
agtaatagga ttaaaagtag aagctatgga aaaattttta tatacagctt cgctatgca    2100 agaattagga tgtaatccaa atcaattttt ctccaaaatc cctcttgagt tgtggacaag    2160
gtataatatg actataaatc aaacaatatg gaatcatgga aatataactt tggggggaatg    2220 gtataaccac accaaagatt tacaaccaaa gttttatgaa ataataatgg acatagaacc    2280
aaataatgta caagggaaaa cagggataca acaattaccc aagtgggaag attgggtaag    2340
atggatagga aatattccac aatatttaaa gggactattg ggaggtatct gggaataggg    2400
attaggagtg ttattattga ttttatgttt acctacattg gttgattgta taagaaattg    2460
tatccacaag atactaggat acacagtaat tgcaatgcct gaagtagaag gagaagaaat    2520
acaaccacaa atggaattga ggagaaatgg tagccaattt ggcatgtctg aaaaagagga    2580
ggaatgatga agtatctcag acttatttta agggagagt actgtgctaa gttcttccct    2640
ttgaggaagg tatgtcatat gaatccattt cgaaccaaat caaactaata agtatgtat    2700 tgtaaggtaa aaggaaaaga caagaagaa gaagaaagaa gaaagctttc aagaggatga    2760
tgacagagtt agaagatcgc ttcaggaagc tatttggcac gacttctaca acgggagaca    2820
gcacagtaga ttctgaagat gaacctccta aaaagaaaa aagggtggac tgggatgagt    2880
attggaaccc tgaagaaata gaaagaatgc ttatggacta gggactgttt acgaacaaat    2940
gataaaagga aatagctaag catgactcat agttaaagcg ctagcagctg cttaaccgca    3000
aaaccacatc ctatgtaaag cttgctaatg acgtataagt tgttccattg taagagtata    3060
taaccagtgc tttgtgaaac ttcgaggagt ctctccgttg aggactttcg agttctccct    3120
tgaggctccc acagatacaa taatatttg agattgaacc ctgtcaagta tctgtgtaat    3180
cttttttacc tgtgaggtct cggaatccgg gccgagaact tcgca                    3225
```

<210> SEQ ID NO 15
<211> LENGTH: 450
<212> TYPE: PRT
<213> ORGANISM: Feline Immunodeficiency Virus

<400> SEQUENCE: 15

-continued

```
Met Gly Asn Gly Gln Gly Arg Asp Trp Lys Met Ala Ile Lys Arg Cys
 1               5                   10                  15

Ser Asn Ala Ala Val Gly Val Gly Gly Lys Ser Lys Lys Phe Gly Glu
             20              25                  30

Gly Asn Phe Arg Trp Ala Ile Arg Met Ala Asn Val Ser Thr Gly Arg
         35                  40                  45

Glu Pro Gly Asp Ile Pro Glu Thr Leu Asp Gln Leu Arg Leu Val Ile
     50                  55                  60

Cys Asp Leu Gln Glu Arg Arg Lys Lys Phe Gly Ser Cys Lys Glu Ile
 65                  70                  75                  80

Asp Lys Ala Ile Val Thr Leu Lys Val Phe Ala Ala Val Gly Leu Leu
                 85                  90                  95

Asn Met Thr Val Ser Ser Ala Ala Ala Glu Asn Met Phe Thr Gln
                 100                 105                 110

Met Gly Leu Asp Thr Arg Pro Ser Met Lys Glu Ala Gly Gly Lys Glu
             115                 120                 125

Glu Gly Pro Pro Gln Ala Phe Pro Ile Gln Thr Val Asn Gly Val Pro
     130                 135                 140

Gln Tyr Val Ala Leu Asp Pro Lys Met Val Ser Ile Phe Met Glu Lys
 145                 150                 155                 160

Ala Arg Glu Gly Leu Gly Gly Glu Glu Val Gln Leu Trp Phe Thr Ala
                 165                 170                 175

Phe Ser Ala Asn Leu Thr Pro Thr Asp Met Ala Thr Leu Ile Met Ala
             180                 185                 190

Ala Pro Gly Cys Ala Ala Asp Lys Glu Ile Leu Asp Glu Ser Leu Lys
             195                 200                 205

Gln Leu Thr Ala Gly Tyr Asp Arg Thr His Pro Pro Asp Ala Pro Arg
     210                 215                 220

Pro Leu Pro Tyr Phe Thr Ala Ala Glu Ile Met Gly Ile Gly Phe Thr
 225                 230                 235                 240

Gln Glu Gln Gln Ala Glu Ala Arg Phe Ala Pro Ala Arg Met Gln Cys
                 245                 250                 255

Arg Ala Trp Tyr Leu Glu Gly Leu Gly Lys Leu Gly Ala Ile Lys Ala
             260                 265                 270

Lys Ser Pro Arg Ala Val Gln Leu Arg Gln Gly Ala Lys Glu Asp Tyr
             275                 280                 285

Ser Ser Phe Ile Asp Arg Leu Phe Ala Gln Ile Asp Gln Glu Gln Asn
     290                 295                 300

Thr Ala Glu Val Lys Leu Tyr Leu Lys Gln Ser Leu Ser Met Ala Asn
 305                 310                 315                 320

Ala Asn Ala Glu Cys Lys Lys Pro Met Thr His Leu Lys Pro Glu Ser
             325                 330                 335

Thr Leu Glu Glu Lys Leu Arg Ala Cys Gln Glu Ile Gly Ser Pro Gly
             340                 345                 350

Tyr Lys Met Gln Leu Leu Ala Glu Ala Leu Thr Lys Val Gln Val Val
         355                 360                 365

Gln Ser Lys Gly Ser Gly Pro Val Cys Phe Asn Cys Lys Lys Pro Gly
     370                 375                 380

His Leu Ala Arg Gln Cys Arg Glu Val Arg Lys Cys Asn Lys Cys Gly
 385                 390                 395                 400

Lys Pro Gly His Val Ala Ala Lys Cys Trp Gln Gly Asn Arg Lys Asn
             405                 410                 415

Ser Gly Asn Trp Lys Ala Gly Arg Ala Ala Pro Val Asn Gln Val
             420                 425                 430
```

```
Gln Gln Ala Val Met Pro Ser Ala Pro Pro Met Glu Glu Lys Leu Leu
        435                 440                 445

Asp Leu
    450

<210> SEQ ID NO 16
<211> LENGTH: 856
<212> TYPE: PRT
<213> ORGANISM: Feline Immunodeficiency Virus

<400> SEQUENCE: 16

Met Ala Glu Gly Phe Ala Ala Asn Arg Gln Trp Ile Gly Pro Glu Glu
 1               5                  10                  15

Ala Glu Glu Leu Leu Asp Phe Asp Ile Ala Thr Gln Met Asn Glu Glu
            20                  25                  30

Gly Pro Leu Asn Pro Gly Met Asn Pro Phe Arg Val Pro Gly Ile Thr
        35                  40                  45

Asp Lys Glu Lys Gln Asp Tyr Cys Asn Ile Leu Gln Pro Lys Leu Gln
 50                  55                  60

Asp Leu Arg Asn Glu Leu Gln Glu Val Lys Leu Glu Glu Gly Asn Ala
 65                  70                  75                  80

Gly Lys Phe Arg Arg Thr Arg Phe Leu Arg Tyr Ser Asp Glu Gln Val
            85                  90                  95

Leu Ser Pro Val His Ala Phe Ile Gly Tyr Cys Ile Tyr Leu Gly Asn
            100                 105                 110

Arg Asn Lys Leu Gly Ser Leu Arg His Asp Ile Asp Ile Glu Ala Pro
            115                 120                 125

Pro Glu Glu Cys Tyr Asp Asn Arg Glu Lys Gly Thr Thr Asp Asn Ile
        130                 135                 140

Lys Tyr Gly Arg Arg Cys Cys Leu Gly Thr Val Thr Leu Tyr Leu Ile
145                 150                 155                 160

Leu Phe Ile Gly Leu Ile Ile Tyr Ser Gln Thr Ala Asp Ala Gln Val
            165                 170                 175

Val Trp Arg Leu Pro Pro Leu Val Val Pro Val Glu Glu Ser Glu Ile
            180                 185                 190

Ile Phe Trp Asp Cys Trp Ala Pro Glu Glu Pro Ala Cys Gln Asp Phe
            195                 200                 205

Leu Gly Ala Met Ile His Leu Lys Ala Lys Thr Asn Ile Ser Ile Arg
        210                 215                 220

Glu Gly Pro Thr Leu Gly Asn Trp Ala Arg Glu Ile Trp Ala Thr Leu
225                 230                 235                 240

Phe Lys Lys Ala Thr Arg Gln Cys Arg Arg Gly Arg Ile Trp Lys Arg
            245                 250                 255

Trp Asp Glu Thr Ile Thr Gly Pro Ser Gly Cys Ala Asn Asn Thr Cys
            260                 265                 270

Tyr Asn Val Ser Ala Ile Val Pro Asp Tyr Gln Arg Tyr Leu Asp Arg
        275                 280                 285

Val Asp Thr Trp Leu Gln Gly Lys Ile Asn Ile Ser Leu Cys Leu Thr
        290                 295                 300

Gly Gly Lys Met Leu Tyr Asn Lys Val Thr Lys Gln Leu Ser Tyr Cys
305                 310                 315                 320

Thr Asp Pro Leu Gln Ile Pro Leu Ile Asn Tyr Thr Phe Gly Pro Asn
            325                 330                 335

Gln Thr Cys Met Trp Asn Thr Ser Gln Ile Gln Asp Pro Glu Ile Pro
            340                 345                 350
```

```
Gln Cys Gly Trp Trp Asn His Met Ala Tyr Tyr Asn Ser Cys Lys Trp
        355                 360                 365

Glu Glu Ala Lys Val Lys Phe His Cys Gln Arg Thr Gln Ser Gln Pro
370                 375                 380

Gly Ser Trp Arg Arg Ala Ile Ser Ser Trp Lys Gln Arg Asn Arg Trp
385                 390                 395                 400

Glu Trp Arg Pro Asp Phe Glu Ser Glu Lys Val Lys Ile Ser Leu Gln
                405                 410                 415

Cys Asn Ser Thr Lys Asn Leu Thr Phe Ala Met Arg Ser Ser Gly Asp
            420                 425                 430

Tyr Gly Glu Val Thr Gly Ala Trp Ile Glu Phe Gly Cys His Arg Asn
        435                 440                 445

Lys Ser Asn Leu His Thr Glu Ala Arg Phe Arg Ile Arg Cys Arg Trp
    450                 455                 460

Asn Val Gly Ser Asp Thr Ser Leu Ile Asp Thr Cys Gly Asn Thr Pro
465                 470                 475                 480

Asn Val Ser Gly Ala Asn Pro Val Asp Cys Thr Met Tyr Ser Asn Lys
                485                 490                 495

Met Tyr Lys Phe Ser Leu Pro Asn Gly Phe Thr Met Lys Val Asp Asp
            500                 505                 510

Leu Ile Met His Phe Asn Met Pro Lys Ala Val Glu Met Asn Asn Ile
        515                 520                 525

Ala Gly Asn Trp Ser Cys Thr Ser Asp Leu Pro Ser Ser Trp Gly Tyr
    530                 535                 540

Met Asn Cys Asn Cys Pro Asn Ser Ser Ser Tyr Ser Gly Thr Lys
545                 550                 555                 560

Met Ala Cys Pro Ser Asn Arg Gly Ile Leu Arg Asn Trp Tyr Asn Pro
                565                 570                 575

Val Ala Gly Leu Arg Gln Ser Leu Glu Gln Tyr Gln Val Val Lys Gln
            580                 585                 590

Pro Asp Tyr Leu Leu Val Pro Glu Val Met Glu Tyr Lys Pro Arg
        595                 600                 605

Arg Lys Arg Ala Ala Ile His Val Met Leu Ala Leu Ala Thr Val Leu
    610                 615                 620

Ser Ile Ala Gly Ala Gly Thr Gly Ala Thr Ala Ile Gly Met Val Thr
625                 630                 635                 640

Gln Tyr His Gln Val Leu Ala Thr His Gln Glu Ser Met Glu Lys Val
                645                 650                 655

Thr Glu Ala Leu Glu Ile Asn Asn Leu Arg Leu Val Thr Leu Glu His
            660                 665                 670

Gln Val Leu Val Ile Gly Leu Lys Val Glu Ala Met Glu Lys Phe Leu
        675                 680                 685

Tyr Thr Ala Phe Ala Met Gln Glu Leu Gly Cys Asn Pro Asn Gln Phe
    690                 695                 700

Phe Ser Lys Ile Pro Leu Glu Leu Trp Thr Arg Tyr Asn Met Thr Ile
705                 710                 715                 720

Asn Gln Thr Ile Trp Asn His Gly Asn Ile Thr Leu Gly Glu Trp Tyr
                725                 730                 735

Asn His Thr Lys Asp Leu Gln Pro Lys Phe Tyr Glu Ile Ile Met Asp
            740                 745                 750

Ile Glu Pro Asn Asn Val Gln Gly Lys Thr Gly Ile Gln Leu Pro
        755                 760                 765
```

```
                                -continued

Lys Trp Glu Asp Trp Val Arg Trp Ile Gly Asn Ile Pro Gln Tyr Leu
    770                 775                 780

Lys Gly Leu Leu Gly Gly Ile Leu Gly Ile Gly Leu Gly Val Leu Leu
785                 790                 795                 800

Leu Ile Leu Cys Leu Pro Thr Leu Val Asp Cys Ile Arg Asn Cys Ile
                805                 810                 815

His Lys Ile Leu Gly Tyr Thr Val Ile Ala Met Pro Glu Val Glu Gly
            820                 825                 830

Glu Glu Ile Gln Pro Gln Met Glu Leu Arg Arg Asn Gly Ser Gln Phe
        835                 840                 845

Gly Met Ser Glu Lys Glu Glu Glu
    850                 855
```

What is claimed is:

1. A recombinant raccoon poxvirus having at least one internal gene comprising a DNA sequence encoding the gag protein of Feline Immunodeficiency Virus (FIV) or immunogenic fragments therefrom.

2. The recombinant raccoon poxvirus of claim 1 wherein said internal gene encodes the FIV gag protein having the amino acid sequence as set out in FIG. 5 or immunogenic fragments therefrom.

3. A vaccine for use in cats comprising:
   a recombinant raccoon poxvirus having at least one internal gene comprising a DNA sequence encoding gag protein of Feline Immunodeficiency Virus (FIV) or immunogenic fragments therefrom, and
   a pharmaceutically acceptable carrier or diluent.

4. The vaccine of claim 3 further comprising a pharmaceutically acceptable adjuvant.

5. The vaccine of claim 3 wherein said internal gene encodes the FIV gag protein having the amino acid sequence as set out in FIG. 5 or immunogenic fragments therefrom.

6. The vaccine of claim 3 further comprising immunogens derived from viruses selected from the group consisting of feline leukemia virus, feline panleucopenia virus, feline rhinotracheitis virus, feline calicivirus, feline infectious peritonitis virus, feline herpesvirus, feline enteric coronavirus, and mixtures thereof.

7. The vaccine of claim 3 further comprising inactivated feline *Chlamydia psittaci,* attenuated feline *Chlamydia psittaci, Microsporum canis,* or mixtures thereof.

8. A vaccine comprising:
   a first recombinant racoon pox virus having at least one internal gene comprising a DNA sequence encoding a member selected from the group consisting of gag proteins of Feline Immunodeficiency Virus (FIV), envelope proteins of Feline Immunodeficiency Virus (FIV) and immunogenic fragments therefrom;
   a second recombinant raccoon pox virus having at least one internal gene comprising a DNA sequence encoding a member selected from the group consisting of gag proteins of Feline Immunodeficiency Virus (FIV), envelope proteins of Feline Immunodeficiency Virus (FIV) and immunogenic fragments therefrom; and
   a pharmaceutically acceptable carrier or diluent.

9. The vaccine of claim 8 further comprising a pharmaceutically acceptable adjuvant.

10. A method for preventing or lessening disease caused by Feline Immunodeficiency Virus (FIV), comprising administering to a feline in need of such treatment a vaccine comprising a recombinant raccoon poxvirus having at least one internal gene comprising a DNA sequence encoding the envelope protein of Feline Immunodeficiency Virus (FIV) or immunogenic fragments therefrom.

11. The method of claim 10 wherein said internal gene encodes the FIV envelope protein having the amino acid sequence as set out in FIG. 3 or immunogenic fragments thereof.

12. A method for preventing or lessening disease caused by Feline Immunodeficiency Virus (FIV), comprising administering to a feline in need of such treatment a vaccine comprising a recombinant raccoon poxvirus having at least one internal gene comprising a DNA sequence encoding the gag protein of Feline Immunodeficiency Virus (FIV) or immunogenic fragments therefrom.

13. The method of claim 12 wherein said internal gene encodes the FIV gag protein having the amino acid sequence as set out in FIG. 5 or immunogenic fragments thereof.

* * * * *

UNITED STATES PATENT AND TRADEMARK OFFICE
CERTIFICATE OF CORRECTION

PATENT NO. : 5,989,562
DATED : November 23, 1999
INVENTOR(S) : Terri WASMOEN, et al.

It is certified that errors appear in the above-identified patent and that said Letters Patent is hereby corrected as shown below:

Title page, Related U.S. Application Data, [62] Divisional application No. 08/482,090, Change filing date "07/07/95" to --06/07/95--.

Signed and Sealed this

Eighteenth Day of July, 2000

Attest:

Q. TODD DICKINSON

*Attesting Officer*     *Director of Patents and Trademarks*